(12) United States Patent (10) Patent No.: US 7,939,091 B2
Coats et al. (45) Date of Patent: May 10, 2011

(54) BIORATIONAL REPELLENTS OBTAINED FROM TERPENOIDS FOR USE AGAINST ARTHROPODS

(75) Inventors: Joel R. Coats, Ames, IA (US); Gretchen Elizabeth Schultz, Ankeny, IA (US); Junwei Zhu, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 1209 days.

(21) Appl. No.: 11/277,122

(22) Filed: Mar. 21, 2006

(65) Prior Publication Data

US 2007/0154504 A1 Jul. 5, 2007

Related U.S. Application Data

(60) Continuation-in-part of application No. 10/323,100, filed on Dec. 18, 2002, now Pat. No. 7,524,888, which is a division of application No. 09/635,030, filed on Aug. 4, 2000, now Pat. No. 6,524,605.

(60) Provisional application No. 60/147,679, filed on Aug. 6, 1999, provisional application No. 60/150,051, filed on Aug. 20, 1999.

(51) Int. Cl.
*A01N 25/32* (2006.01)
*A01N 31/06* (2006.01)
(52) U.S. Cl. ............... 424/406; 424/195.18; 424/405; 424/736; 424/DIG. 10; 514/729; 514/919
(58) Field of Classification Search .......... None
See application file for complete search history.

(56) References Cited

U.S. PATENT DOCUMENTS

| 4,735,358 | A | 4/1988 | Morita et al. |
| 4,882,873 | A | 11/1989 | Purnell |
| 5,662,914 | A | 9/1997 | Shorey et al. |
| 5,750,129 | A | 5/1998 | Wakarchuk |

(Continued)

FOREIGN PATENT DOCUMENTS

FR 2622103 4/1989

(Continued)

OTHER PUBLICATIONS

Isman,Murray -Pesticide Outlook pp. 68-72,Apr. 1999 "Pesticides Based on Plant Essentila Oils".*

(Continued)

*Primary Examiner* — Neil Levy
(74) *Attorney, Agent, or Firm* — Schwegman, Lundberg & Woessner, P.A.

(57) ABSTRACT

The compositions comprise an effective repellent amount of one or more monoterpenoids, one or more sesquiterpenoids or a blend of one or more monoterpenoids and one or more sesquiterpenoids in combination with a carrier, wherein the compositions are formulated to repel a target pest from a target area. In one embodiment, the one or more monoterpenoids, and/or one or more sesquiterpenoids are from a biorational source, such as a plant volatile. In one embodiment, the one or more sesquiterpenoids are oxygen-containing sesquiterpenoids. In a particular embodiment, the plant volatile is a monoterpenoid, such as "nepetalactone" (or the individual nepetalactone isomers) derived from catnip (*Nepeta cataria*). In another embodiment, the plant volatile is additionally or alternatively a sesquiterpenoid derived from the fruit of the Osage orange tree (*Maclura pomifera*), Siam wood or the *Amyris* plant. Such compositions have repellency, including long term repellency, against arthropods.

5 Claims, 9 Drawing Sheets

U.S. PATENT DOCUMENTS

| | | | |
|---|---|---|---|
| 6,337,071 | B1 | 1/2002 | Molyneux |
| 6,524,605 | B1 | 2/2003 | Coats et al. |
| 7,453,024 | B2 * | 11/2008 | Aharoni et al. .......... 800/298 |
| 7,524,888 | B2 | 4/2009 | Coats et al. |
| 2003/0138471 | A1 | 7/2003 | Coats et al. |
| 2004/0103388 | A1 | 5/2004 | Aleshin et al. |

FOREIGN PATENT DOCUMENTS

| | | |
|---|---|---|
| FR | 2697133 | 4/1994 |
| JP | 10-22807 | 1/1989 |
| JP | 6-16503 | 1/1994 |
| JP | 2004-51564 | 2/2004 |
| WO | WO-94/05151 A1 | 3/1994 |
| WO | WO-2004082358 A2 | 9/2004 |
| WO | WO-2004103388 A2 | 12/2004 |

OTHER PUBLICATIONS

Ahmad, F. B., et al., "Chemical Constituents of the Essentials Oils of *Goniothalamus uvariodes* King", *Flavour and Fragrance J.*, vol. 18, (2003),128-130 pgs.

Kayser, O. , et al., "Composition of the essential oils of *Pelargonium sidoides* DC. and *Pelargonium reniforme* Curt", *Flavour and Fragrance J.*, vol. 13, (1998),209-212 pgs.

Matsuda, B. M., et al., "Essential Oil Analysis and Field Evaluation of the Citrosa Plant *Pelargonium citrosum* As a Repellent Against Populations of *Aedes* Mosquitoes", *Journal of the American Mosquito Control Association*,12(1), (1996),69-74.

Trongtokit, Y. , et al., "Comparative Repellency of 38 Essential Oils Against Mosquito Bites", *Phytotheraphy Research*, John Wiley & sons Ltd. Chichester, GB, vol. 19, No. 4, Issn: 0951-418X,(Apr. 2005),303-309 pgs.

Van Beek, T. A., et al., "Preparative Isolation of (+)-Beta-Eudesmol from *Amyris balsamifera*", *Chromatographia*, 28(3/4), (Aug. 1989),126-128.

Bernier, U. R., et al., "Chapter 4. Human Emanations and Related Natural Compounds That Inhibit Mosquito Host-Finding Abilities", *In: Insect Repellents: Principles, Methods, and Uses*, Debboun, M., et al., Editors, CRC Press, Taylor & Francis Group, Boca Raton, FL, (2006), 77-100.

Bernier, U. R., et al., "Comparison of Contact and Spatial Repellency of Catnip Oil and N, N-Diethyl-3-methylbenzamide (Deet) Against Mosquitoes", *J. Med. Entomol.*, 42(3), (2005), 306-311.

Carroll, J. F., et al., "Comparative Activity of Deet and AI3-37220 Repellents Against the Ticks *Ixodes scapularis* and *Amblyomma americanum* (Acari: Ixodidae) in Laboratory Bioassays", *Journal of Medical Entomology*, 41(2), (2004), 249-254.

Dogan, E. B., et al., "Behavioural Mode of Action of Deet: Inhibition of Lactic Acid Attraction", *Medical and Veterinary Entomology*, 13, (1999), 97-100.

Grieco, J. P., et al., "A Novel High-Throughput Screening System to Evaluate the Behavioral Response of Adult Mosquitoes to Chemicals", *Journal of the American Mosquito Control Association*, 21(4), (2005), 404-411.

Hoskins, W. M., et al., "The Olfactory Responses of Flies in a New Type of Insect Olfactometer I. Theory and Design of the Olfactometer", *Journal of Economic Entomology*, 27(5), (1934), 1029-1036.

Miller, J. R., et al., "Sustained-Flight Tunnel for Measuring Insect Responses to Wind-Borne Sex Pheromones", *Journal of Chemical Ecology*, 4(2), (1978), 187-198.

Schultz, G., et al., "Chapter 13—Natural Insect Repellents: Activity Against Mosquitos and Cockroaches", *In: Natural Products for Pest Management. ACS Symposium Series #927*, American Chemical Society, Washington, D.C.,(2006), 168-181.

Waka, M., et al., "The Effect of Repellents *Ocimum forskolei* and Deet on the Response of *Anopheles stephensi* to Host Odours", *Medical and Veterinary Entomology*, 20, (2006), 373-376.

Wieting, J., et al., "The Olfactory Responses of Flies in a New Type of Insect Olfactometer II. Responses of the Housefly to Ammonia, Carbon Dioxide and Ethyl Alcohol", *Journal of Economic Entomology*, 32(1), (Feb. 1939), 24-28.

"New uses for catnip oil, repelling mosquitoes!", http://web.archive.org/web/20011217083424/http://www.kookykat.com/new_page_1.htm, (1995),3 pgs.

Adler, V. E., et al., "Evaluation of Selected Natural and Synthetic Products as House Fly Repellents", *J. Environ. Sci. Health*, A17(5), (1982),667-673.

Aldrich, J. R., et al., "Male-Specific Volatiles from Nearctic and Australasian True Bugs (Heteroptera: Coreidae and Alydidae)", *Journal of Chemical Ecology*, 19, (1993),2767-2781.

Aldrich, J. R., et al., "Natural Products of Abdominal and Metathoracic Scent Glands of Coreoid Bugs", *Annals of the Entomological Society of America*, 68, (Nov. 1975),955-960.

Appel, A. G., et al., "Repellency of Milled Aromatic Eastern Red Cedar to Domiciliary Cockroaches (Dictyoptera: Blattellidae and Blattidae)", *Journal of Economic Entomologgy*, 82, (Feb. 1989),152-155.

Baker, J. T., et al., "The volatile constituents of the scent gland reservoir of the fruit-spotting bug, *Amblypelta nitida*", *Aust. J. Chem.*, 25, (1972),393-400.

Bates, R. B., et al., "Terpenoids. Cis-trans- and trans-cis-Nepetalactones", *Experientia*, 19, (1963),564-565.

Beavers, J B., et al., "Synthetic Attractants for Some Dipteran Species", *Journal of Economic Entomology*, 65, (Dec. 1972),1740-1741.

Black, J. W., "Nepetalactone: scores purrfect with cats!", *Chem 13 News*, (Jan. 1995),12-13.

Bodenstein, O F., et al., *Laboratory Evaluations of Compounds as Repellents to Cockroaches, 1953-1974: Production Research Report No. 164*, Agricultural Research Service, United States Department of Agriculture,(1976),1-28.

Burden, G. S., "Repellancy of Selected Insecticides," *Pest Control*, (1975),pp. 16, 18.

Carle, S. A., et al., "Variation in Host Fruit Volatiles Attractive to Apple Maggot Fly, *Rhagoletis pomonella*", *Journal of Chemical Ecology*, 13, (1987),795-805.

Charles, D J., et al., "Essential Oil Constituents of *Ocimum micranthum* Willd", *J. Agric. Food Chem.*, 38, (1990),120-122.

Coats, J. R., et al., "Toxicity and Neurotoxic Effects of Monoterpenoids in Insects and Earthworms", *Naturally Occurring Pest Bioregulators*, Hedlin, P.A., (ed.), Chapter 20, ACS Symposium Series: 449,,(1991),305-316.

Das, Y.T. , et al., "Non-Repellency of Two Insect Growth Regulators with Juvenile Hormone Activity to *Blattella germanica*", *Ent. Exp. & Appl.*, 20, (1976),195-198.

Davis, E. E., et al., "Lactic Acid-sensitive Receptors on the Antennae of the Mosquito, *Aedes aegypti*", *Journal of Comparative Physiology A*, 105(1), (1976),43-54.

Deb-Kirtaniya, S. , et al., "Extracts of Garlic as Possible Source of Insecticides", *Indian J. Agric. Sci.*, 50, (Jun. 1980),507-510.

Edwards, D. L., et al., "Insect-Repellent-Induced Toxic Encephalopathy in a Child", *Clinical Pharmacy*, 6, (Jun. 1987),496-498.

Eisenbraun, E. J., et al., "Structure and Stereochemistry 4a(beta),7(alpha),7a(beta)-Nepetalactone from *Nepeta mussini* and Its Relationship to the 4a(alpha),7(alpha),7a(alpha)- and 4a(alpha),7(alpha),7a(beta)-Nepetalactones from *N. cataria*", *J. Org. Chem.*, 45, (1980),3811-3814.

Eisner, T. , "Catnip: Its Raison d'Etre", *Science*, 146 (Dec. 1964),1318-1320.

Fradin, M. S., et al., "Comparative Efficacy of Insect Repellents Against Mosquito Bites", *The New England Journal of Medicine*, 347(1), (Jul. 4, 2002),13-18.

Handjieva, N. V., et al., "Constituents of Essential Oils from *Nepeta cataria* L., *N. grandiflora* M.B. and *N. nuda* L.", *J. Essent. Oil Res.*, 8, (Nov./Dec. 1996),639-643.

Hernandez, M. M., et al., "Electroantennogram Activity from Antennae of *Ceratitis capitata* (Wied.) to Fresh Orange Airborne Chemical Volatiles", *Journal of Chemical Ecology*, 22, (1996),1607-1619.

Inazuka, S. , "Monoterpenoids as Repellents Against the German Cockroach (*Blattella germanica* L.)", *Journal of Pesticide Science*, 8, abstract in English,(Aug. 1983),293-299.

Inazuka, S., "New Methods of Evaluation for Cockroach Repellents and Repellency of Essential Oils Against German Cockroach (*Blattella germanica* L.)", *Journal of Pesticide Science*, 7, abstract in English,(May 1982),133-143.

Jain, T. C., et al., "Thermolysis of Elemol: Silver (I) Ion Catalyzed Conversion of Elemol to Eudesmols", *Tetrahedron Letters*, 50, (1972),5139-5142.

Karr, L. L., et al., "Insecticidal Properties of d-Limonene", *J. Pesticide Sci.*, 13, (1988),pp. 287-290.

Karr, L L., et al., "Repellency of Dried Bay Leaves (*Lauris nobilis*), Wrigley's Spearmint Chewing Gum, Raw Osage Orange Fruit (*Maclura pomifera*), and Extracts of Osage Orange Fruit to the German Cockroach, 1989", *Insecticide & Acaricide Tests*, 17, (1992),p. 393.

Kaul, V. K., et al., "Essential Oil Composition of *Bothriochloa pertusa* Phyletic Relationship in Aromatic Grasses", *Biochemical Systematics and Ecology*, 26, (1998),347-356.

Klowden, M J., et al., "Role of the Fat Body in the Regulation of Host-Seeking Behaviour in the Mosquito, *Aedes aegypti*", *Journal of Insect Physiology*, 33, (1987),643-646.

Leach, G. J., et al., "Some Cardiovascular Effects of the Insect Repellent N,N-Diethyl-m-Toluamide (DEET)", *Journal of Toxicology and Environmental Health*, 25, (1988),217-225.

Lewis, D. J., et al., "Evaluation of an Electronic Mosquito Repeller", *The Canadian Entomologist*, 114, (Aug. 1982),699-702.

Lindsay, L. R., et al., "Evaluation of the Efficacy of 3% Citronella Candles and 5% Citronella Incense for Protection Against Field Populations of *Aedes* Mosquitoes", *Journal of the American Mosquito Control Association*, (1996),293-294.

Mattheis, J. P., et al., "Identification of Headspace Volatile Compounds from 'Bing' Sweet Cherry Fruit", *Phytochemistry*, 31, (1992),775-777.

Mauer, D. J., et al., "Attraction of Culex pipiens pipiens (Diptera: Culicidae) to Flower Volatiles", *Journal of Medical Entomology*, 36, (Jul. 1999),503-507.

Maugh, T. H., "To Attract or Repel, That is the Question", *Science*, 218, (Oct. 15, 1982),p. 278.

McElvain, S M., et al., "The Constituents of the Volatile Oil of Catnip. I. Nepetalic Acid, Nepetalactone and Related Compounds", *Journal of American Chemistry Society*, 63, (Jun. 1941),1558-1563.

Miller, J D., "Anaphylaxis Associated with Insect Repellent", *The New England Journal of Medicine*, 307, (1982),1341-1342.

Ndungu, M , et al., "*Cleome monophylla* Essential Oil and its Constituents as Tick (*Rhipicephalus appendiculatus*) and Maize Weevil (*Sitophilus zeamais*) Repellents", *Entomologia Experimentalis et Applicata*, 76, (1995),217-222.

Osimitz, T. G., et al., "The Present Safety Assessment of DEET", *Journal of the American Mosquito Control Association*, 11, (1995),274-278.

Peterson, C J., et al., "Behavioral activity of catnip (Lamiaceae) essential oil components to the German cockroach (Blattodea: Blattellidae)", *Journal of Economic Entomology*, 95, (2002),377-380.

Peterson, C., et al., "Identification of Components of Osage Orange Fruit (*Maclura pomifera*) and Their Repellency to German Cockroaches", *Journal of Essential Oil Research*, 14, (2002),233-237.

Peterson, C J., et al., "Osajin and Pomiferin, Two Isoflavones Purified from Osage Orange Fruits, Tested for Repellency to the Maize Weevil (Coleoptera: Curculionidae)", *Environmental Entomology*, 29, (2000),1133-1137.

Porter, N G., et al., "Chemical, physical and antimicrobial properties of essential oils of *Leptospermum scoparium* and *Kunzea ericoides*", *Phytochemistry*, 50, (Feb. 10, 1999),407-415.

Qiu, H , et al., "Pharmacokinetics, Formulation, and Safety of Insect Repellent N,N-Diethyl-3-Methylbenzamide (DEET): A Review", *Journal of the American Mosquito Control Association*, 14, (Mar. 1998),12-27.

Regnier, F. E., et al., "The Biosynthesis of Methylcyclopentane Monoterpenoids-II", *Phytochemistry*, 7, (1968),221-230.

Robbins, P. J., et al., "Review of the Biodistribution and Toxicity of the Insect Repellent N,N-Diethyl-m-Toluamide (DEET)", *Journal of Toxicology and Environmental Health*, 18, (1986),503-525.

Roland, E. H., et al., "Toxic Encephalopathy in a Child after brief Exposure to Insect Repellents", *Can. Med. Assoc. J.*, 132, (Jan. 15, 1985),155-156.

Rowley, W. A., et al., "A Microcomputer-Monitored Mosquito Flight Activity System", *Annals of the Entomological Society of America*, 80, (Jul. 1987),534-538.

Sakan, T. , et al., "The Synthesis of dl-Nepetalactone", *Bull. Chem. Soc. Jpn.*, 33, (Dec. 1960),1737-1738.

Sakho, M. , et al., "Enzymatic Maceration: Effects on Volatile Components of Mango Pulp", *Journal of Food Science*, 63, (1998),975-978.

Sakuma, M. , et al., "The Linear Track Olfactometer: An Assay Device for Taxes of the German Cockroach, *Blattella germanica* (L.) (Dictyoptera : Blattellidae) toward their Aggregation Pheromone", *Appl. Ent. Zool*, 20,(1985),387-401.

Sand, Susan , "A tree history—the osage orange", *American Horticulturalist*, 70, (1991),37-39.

Scheffler, I , et al., "Behavioural Responses of German Cockroaches (*Blattella germanica* L.) Induced by Plant Repellents", *In: Insecticides: Mechanism of Action and Resistance*, Otto, D., et al. (eds.), Intercept Ltd., Andover, England,(1992),107-116.

Schultz, G. , et al., "Catnip and Osage Orange Essential Oil Effect on *Culex pipiens* L. (Diptera: Culicidae) in a Static-Air Olfactometer", *Proceedings of the 226th ACS National Meeting*, New York, Poster,(Sep. 7-11, 2003),1 p.

Schultz, G , et al., "Catnip, *Nepeta cataria* (Lamiales: Lamiaceae)—A Closer Look: Seasonal Occurrence of Nepetalactone Isomers and Comparative Repellency of Three Terpenoids to Insects", *Environ. Entomol.*, 33, (2004),1562-1569.

Schultz, G., et al., "Repellency of Catnip and Osage Orange Essential Oils to Two Mosquito Species", *Proceedings of the 228th ACS National Meeting*, Washington, D.C., Poster,(Aug. 28-Sep. 1, 2005),1 p.

Schultz, G. , et al., "Seasonal Variation of Nepetalactone Isomers Found in Catnip, *Nepeta cataria*", *Proceedings of the 57th Annual Meeting of the Entomological Society of America, North Central Branch*, East Lansing, MI, Poster,(Mar. 2005),1 p.

Sharma, V P., et al., "Mosquito Repellent Action of Neem (*Azadirachta indica*) Oil", *Journal of the American Mosquito Control Association*, 9, (1993),359-360.

Simbro, E. J., et al., "Repellent Activity of Catnip and Osage Orange Components against American Cockroaches", *Proceedings of the 57th Annual Meeting of the Entomological Society of America, North Central Branch*, East Lansing, MI, Poster,(Mar. 2002),1 p.

Simbro, E. J., et al., "Repellent Activity of Catnip to the American Cockroach, Housefly, and Mosquito", *Proceedings of the 56th Annual Meeting of the Entomological Society of America, North Central Branch*, Fort Collins, CO, abstract No. D26,(Mar. 25-28, 2001),p. 8.

Singh, D. , et al., "Repellent and Insecticidal Properties of Essential Oils Against Housefly, *Musca domestica* L", *Insect Sci. Applic.*, 12, (1991),487-491.

Smith, C. N., et al., "Effectiveness of Repellents Applied to Clothing", *Journal of Economic Entomology*, 42, (1949),439-440.

Smith, R. M., et al., "Iridodials and Nepetalactone in the Defensive Secretion of the Coconut Stick Insects, *Graeffea crouani*", *Journal of Chemical Ecology*, 5, (1979),727-735.

Snook, M. E., et al., "Caffeoyltartronic Acid from Catnip (*Nepeta cataria*): A Precursor for Catechol in Lubber Grasshopper (*Romalea guttata*) Defensive Secretions", *Journal of Chemical Ecology*, 19, (1993),1957-1966.

Snyder, J. W., et al., "Acute Manic Psychosis Following the Dermal Application of N,N-Diethyl-M-Toluamide (DEET) in an Adult", *Clinical Toxicology*, 24, (1986),429-439.

Steltenkamp, R. J., et al., "Alkyl and Aryl Neoalkanamides: Highly Effective Insect Repellents", *Journal of Medical Entomology*, 29, (Mar. 1992),141-149.

Sugawara, R. , et al., "Attraction of Several Dipterous Insects to Aliphatic Esters (Diptera : Milichiidae, Chloropidae and Ceratopogonidae)", *Appl. Ent. Zool.*, 9, (1974),11-18.

Sugawara, R , et al., "Attraction of the German Cockroach to Cyclohexyl Alkanoates and n-Alkyl Cyclohexaneacetates", *J. Insect Physiol*, 21, (1975),957-964.

Veltri, J., et al., "Retrospective analysis of calls to poison control centers resulting from exposure to the insect repellent N,N-diethyl-m-toluamide (DEET) from 1985-1989", *Clinical Toxicology*, 32, (1994),1-16.

Von Mayenburg, J, et al., "Contact Urticaria to Diethyltoluamide", *Contact Dermatitis*, 9, (1983),p. 171.

Watanabe, K., et al., "New Mosquito Repellent from *Eucalyptus camaldulensis*", *J. Agric. Food Chem.*, 41, (1993),2164-2166.

Weyerstahl, P., et al., "Constituents of Vietnamese Pemou Oil—A Reinvestigation", *Flavour and Fragrance Journal*, 14, (1999),409-410.

Williams, R. N., et al., "Rose Chafer (Coleoptera: Scarabaeidae): Improved Attractants for Adults", *Journal of Economic Entomology*, 83, (Feb. 1990),111-116.

Zadikoff, C M., "Toxic encephalopathy associated with use of insect repellant", *Journal of Pediatrics*, 95, (Jul. 1979),140-142.

"U.S. Appl. No. 10/323,100 Supplemental Notice of Allowability mailed Nov. 12, 2008", 4 pgs.

"U.S. Appl. No. 10/323,100 Notice of Allowance mailed Aug. 12, 2008", 4 pgs.

"U.S. Appl. No. 11/932,649 Non-Final Office Action mailed Jan. 30, 2009", 11 pgs.

"International Application Serial No. PCT/US2007/064537 International Preliminary Report on Patentability Oct. 22, 2008", 23 pgs.

"U.S. Appl. No. 10/323,100, Response filed Apr. 16, 2008 to Non-Final Office Action mailed Nov. 16, 2007.", 9 pgs.

"International Application Serial No. PCT/US2007/064537, Written Opinion mailed May 19, 2008", 13 pgs.

"International Application Serial No. PCT/US2007/064537, International Search Report mailed May 19, 2008", 10 pgs.

"Kalyx.com—Certificate of Analysis—Organic Amyris Oil", [online]. [retrieved Jun. 7, 2004]. Retrieved from the Internet: <URL: http://www.kalyx.com/catalog/eoamyris.htm>, (2004), 2 pgs.

Chantraine, M., et al., "Insecticidal Activity of Essential Oils on *Aedes aegypti* Larvae", *Phytotherapy Res.*, 12, (1998), 350-354.

Cheng, S. S., et al., "Antitermitic and Antifungal Activities of Essential Oil of *Calcocedrus formosana* Leaf and its Composition", *J. Chem. Ecology*, 10, (2004), 1957-1967.

Derwent Publications, "Cockroach Repellent Comprising Natural Ingredients", *Database Record* No. AN-1996-217126, (Abstract for JP-8-81306), (1996), 1 pg.

Derwent Publications, "Insect Repellent Contg. Cadinen-type Sesqui", *Database Record* No. AN 1994-061953, (Abstract for JP-6-16503), (1994), 1 pg.

Derwent Publications, "Pest Repellent Foot Band for Protecting Human Body from Creeping or Flying Insect Pests", *Database Record* No. AN 2004-185601, (Abstract for JP-2004-51564),(2004), 1 pg.

Derwent Publications, "Termite Expellant", *Database Record* No. AN 1989-071644, (Abstract for JP-10-22807),(1989),1 pg.

Grace, M. H., "Chemical Composition and Biological Activity of the Volatiles of *Anthemis melampodina* and *Pluchea dioscoridis*", *Phytotherapy Research*, 16,(2002), 183-185.

Hadjiakhoondi, A., et al., "Chemical Constituents and Efficacy of *Cymbopogon olivieri*(Boiss). Bar Essential Oil Against Malaria Vector,*Anopheles stephensi*", (Abstract Only), *Daru. J. Faculty of Pharmacy*, 11(3), (2003), 2 pgs.

Kinjo, K., et al., "Termiticidal Substances from the Wood of *Chamaecyparis obtusa* Endl", *Mokuzai Gakkaishi*, 34(5), (Abstract Only),(1988), 1 pg.

Lesueur, D., et al., "Analysis of the Root Oil of *Fokienia hodginsii* (Dunn) Henry et Thomas (Cupressaceae) by GC,GC-MS and $^{13}$C NMR", *Flavour and Fragrance J.*, 21, (Jan. 2006), 171-174.

Sajjadi, S. E., "Analysis of the Essential Oil of *Nepeta sintenisii* Bornm. from Iran", *Daru,J.Faculty of Pharmacy*, 13(2), (2005), 61-64.

Van Beek, T. A., et al., "Essential Oil of *Amyris balsamifera*", *Phytochemistry*, 28(7), (1989), 1909-1911.

Watanabe, P., et al., "Termite Repellent Sesquiterpenoids from *Callitris glaucophylla* Heartwood", *Journal of Wood Science*, 51(5), (2005), 514-519.

Weyerstahl, P., et al., "Constituents of Vietnamese Pemou Oil—A Reinvestigation", *Flavour and Fragrance J.*, 14, (1999), 409-410.

"U.S. Appl. No. 10/323,100, Final Office Action mailed Apr. 14, 2006", 7.

"U.S. Appl. No. 10/323,100, Response Final Office Action Aug. 14, 2006 to Final office Action mailed Apr. 14, 2006", 15.

"U.S. Appl. No. 10/323,100 Non-Final Office Action mailed Oct. 27, 2006", 7.

"U.S. Appl. No. 10/323,100 Response Filed Feb. 27, 2007 to Non-Final Office Action mailed Oct. 27, 2007", 48.

"U.S. Appl. No. 10/323,100, Non-Final Office Action mailed Oct. 7, 2005", 5.

"U.S. Appl. No. 10/323,100, Non-Final Office Action mailed Jun. 5, 2007", 6.

"U.S. Appl. No. 10/323,100, Non-Final Office Action mailed Jun. 7, 2005", 5.

"U.S. Appl. No. 10/323,100, Response filed Jul. 7, 2005 to Non-Final Office Action mailed Jun. 7, 2005", 6.

"U.S. Appl. No. 10/323,100,Response filed Jan. 5, 2006 to Non-Final Office Action mailed Oct. 7, 2005", 10.

"U.S. Appl. No. 09/635,030 Final Office Action mailed Apr. 10, 2002", 6.

"U.S. Appl. No. 09/635,030 First Office Action Mar. 13, 2001", 7.

"U.S. Appl. No. 09/635,030 Non-Final Office Action mailed Sep. 25, 2001", 8.

"U.S. Appl. No. 09/635,030 Notice of Allowance mailed Sep. 24, 2002", 6.

"U.S. Appl. No. 09/635,030 Response filed Dec. 19, 2001 to Non-Final Office Action mailed Sep. 25, 2001", 3.

"U.S. Appl. No. 09/635,030 Response filed Jul. 11, 2001 to First Office Action mailed Mar. 13, 2001", 15.

"U.S. Appl. No. 09/635,030 Response filed Jul. 9, 2002 to Final Office Action mailed Apr. 10, 2002", 4.

"U.S. Appl. No. 10/323,100, Final Office Action mailed Aug. 21, 2006", 15.

Clegern, Robert, W., "Population dynamics and environmental stress studies of house files in the laboratory", *Thesis for the degree of Doctor of Philosophy in Entomology in the Graduate College of the University of Illinois at Urbana-Champain*, (1972),1-151.

"U.S. Appl. No. 09/635,030, Notice of Allowance mailed Sep. 24, 2002", 8 pgs.

"U.S. Appl. No. 09/635,030, Response filed Jul. 9, 2002 to Non Final Office Action mailed Apr. 10, 2002", 4 pgs.

"U.S. Appl. No. 09/635,030, Response filed Jul. 11, 2001 to Non Final Office Action mailed Mar. 13, 2001", 24 pgs.

"U.S. Appl. No. 09/635,030, Response filed Dec. 19, 2001 to Restriction Requirement mailed Sep. 25, 2001", 6 pgs.

"U.S. Appl. No. 09/635,030, Restriction Requirement Received mailed Sep. 25, 2001", 8 pgs.

"U.S. Appl. No. 09/635,030, Non Final Office Action mailed Mar. 13, 2001", 14 pgs.

"U.S. Appl. No. 10/323,100, Response filed Aug. 31, 2007 to Non Final Office Action mailed Jun. 6, 2007", 24 pgs.

"U.S. Appl. No. 10/323,100, Final Office Action mailed Apr. 14, 2006", 7 pgs.

"U.S. Appl. No. 10/323,100, Non Final Office Action mailed Jun. 6, 2007", 6 pgs.

"U.S. Appl. No. 10/323,100, Non Final Office Action mailed Oct. 7, 2005", 5 pgs.

"U.S. Appl. No. 10/323,100, Non Final Office Action mailed Oct. 27, 2006", 7 pgs.

"U.S. Appl. No. 10/323,100, Non Final Office Action mailed Nov. 16, 2007", 7 pgs.

"U.S. Appl. No. 10/323,100, Preliminary Amendment filed Dec. 18, 2002", 1 pg.

"U.S. Appl. No. 10/323,100, Response filed Jan. 5, 2006 to Non Final Office Action mailed Oct. 7, 2005", 10 pgs.

"U.S. Appl. No. 10/323,100, Response filed Feb. 22, 2007 to Non Final Office Action mailed Oct. 27, 2006", 24 pgs.

"U.S. Appl. No. 10/323,100, Response filed Jul. 7, 2005 to Restriction Requirement mailed Jun. 7, 2005", 6 pgs.

"U.S. Appl. No. 10/323,100, Response filed Aug. 14, 2006 to Final Office Action mailed Apr. 14, 2006", 15 pgs.

"U.S. Appl. No. 10/323,100, Restriction Requirement mailed Jun. 7, 2005", 5 pgs.

"U.S. Appl. No. 10/323,100 Non-Final Office Action mailed Nov. 16, 2007", 9 Pages.

"U.S. Appl. No. 09/635,030, Non Final Office Action mailed Apr. 10, 2002", 6 pgs.

* cited by examiner

*-LESS THAN 80% MATCH QUALITY

BIORATIONAL REPELLENTS OBTAINED FROM TERPENOIDS FOR USE AGAINST ARTHROPODS

This application is a continuation-in-part of U.S. application Ser. No. 10/323,100 filed on Dec. 18, 2002, now U.S. Pat. No. 7,524,888 which is a divisional of U.S. application Ser. No. 09/635,030 filed on Aug. 4, 2000, now issued as U.S. Pat. No. 6,524,605. U.S. Pat. No. 6,524,605 claims the benefit under 35 U.S.C. 119 (e) of U.S. Provisional Application Ser. No. 60/147,679 filed on Aug. 6, 1999, now abandoned, and U.S. Provisional Application Ser. No. 60/150,051 filed on Aug. 20, 1999, now abandoned, all of which are hereby incorporated by reference in their entirety.

STATEMENT OF GOVERNMENT RIGHTS

This invention was made with support of the United States Government under USDA/SCREES 2001-31100-06019; 2002-31100-06019; 2003-31100-06019; 2004-31100-06019, and 2005-31100-06019. The Government has certain rights in this invention.

FIELD

The present invention relates to repellents, and, in particular to natural insect repellents obtained from terpenoids

BACKGROUND

The use of insect repellents is widely accepted throughout the world. Besides repellents intended for outdoor use, repellents are also available for use in homes to repel pests such as cockroaches, termites, ants, fleas, and so forth. The commercial standard for insect repellency is N,N-diethyl-3-methylbenzamide (DEET). The U.S. Environmental Protection Agency (EPA) estimates that more than 38% of the U.S. population uses a DEET-based insect repellent every year and that worldwide use exceeds 200,000,000 people annually (U.S. Environmental Protection Agency, PBS1-207722, 1980). However, DEET is known to cause severe adverse health effects in some people, particularly in higher concentrations. (See, for example, Qui et. al., 1998, *J. Am. Mosq. Control Assoc.* 14 (1):12-27; Miller, J. D., 1982, *New Eng. J. Med.* 307:1341-1342; Roland, et. al., 1985, *Can. J. Med. Assn. J.* 132:155-156).

Over the last several years effort has been directed toward the development of natural repellents. Much of this initiative is due not only to the toxic effects of traditional repellents, but to increased government regulation of certain chemicals in insect pest management (e.g., DEET, naphthalene, dimethyl phthalate, etc.) and the desire to use products which are more environmentally friendly than traditional chemicals.

Naturally derived biorepellents have been investigated as a group of chemicals that have biological activity and can cause repellent or insecticidal effects without negative impacts on human safety or the environment. Many plant oils and extracts have been identified as insect deterrents, repellents or toxins. These include botanical insect repellents which include components extracted from citronella, cinnamon, cedar, eucalyptus, mints, lemongrass, geranium, and soybean. Neem oil, an extract of the Neem tree, *Azadirachta indica*, is another natural product that has shown repellency of *Anopheles* mosquitoes. However, these products do not offer residual control equivalent to standards, such as DEET. Citronella, for example, is known to be weakly repellent and highly volatile. Citronella candles have been shown to be marginally effective, if at all.

Thus, what is needed is a biorepellent without toxic or environmental concerns, but which can provide effective repellency against target pests.

SUMMARY

Repellent compositions containing monoterpenoids and/or sesquiterpenoids are disclosed. Repellent compositions comprising an effective amount of one or more monoterpenoids and/or one or more sesquiterpenoids effective to repel a target pest from a target area, the one or more monoterpenoids and/or one or more sesquiterpenoids in combination with a carrier is disclosed. In one embodiment, a repellent composition comprising an effective repellent amount of an oxygen-containing sesquiterpenoid and a monoterpenoid blend in combination with a carrier, wherein the composition is formulated to repel a target pest from a target area is disclosed. In one embodiment, a repellent composition comprising an effective repellent amount of a sesquiterpenoid selected from the group consisting of *Amyris* essential oil, Siam wood essential oil, (E)-nerolidol and fokienol to repel a target pest from a target area, the sesquitepemoid in combination with a carrier is disclosed In one embodiment, the one or more monoterpenoids and/or one or more sesquiterpenoids are from a biorational source, such as a plant volatile. In a particular embodiment, the plant volatile is a monoterpenoid, such as "nepetalactone" (or the individual nepetalactone isomers, namely Z,E-nepetalactone and E,Z-nepetalactone) derived from catnip (*Nepeta cataria*). In one embodiment, the plant volatile is any one or a combination of sesquiterpenoids derived from the fruit of the Osage orange tree (*Maclura pomifera*), Siam wood (*Fokeinia*) or the West Indian sandalwood tree (*Amyris balsamifera*, also known as the "*Amyris* plant").

Yet other embodiments include combinations of one or more monoterpenoid plant volatiles and one or more sesquiterpenoid plant volatiles. In yet other embodiments, components such as p-menthane diol, cinnamic alcohol, wintergreen and/or citronella, and the like, are used in combination with one or more sesquiterpenoids.

The novel compositions described herein have repellency against arthropods, such as cockroaches, mosquitoes, mites, ticks, spiders, and so forth. Embodiments of the invention further include methods of repelling target pests from a target area comprises applying an effective amount of a composition comprising the compound together with a suitable carrier in or near a target area, including applying the composition directly onto humans, animals (e.g., pets, livestock), and so forth. Repellents can also be applied to other target areas, including, but not limited to, plants, articles of clothing, tents, sleeping bags, pillows, bed nets, blankets, premises, etc. In one embodiment, a method for repelling a target pest from a target area, comprising applying an effective repelling amount of a composition in or around the target area, the composition comprising a monoterpenoid/sesquiterpenoid blend or a sesquiterpenoid and a carrier is disclosed. In one embodiment, the compositions exhibit long term repellency, i.e., in excess of two (2) hours. In one embodiment, a method for providing long term repellency from a target area comprising applying an effective repelling amount of a composition in or around the target area, the composition comprising a monoterpenoid or a sesquiterpenoid and a carrier, wherein target pests are repelled in excess of two hours is disclosed.

It has also been determined that the chemoreceptors responsible for repellent response are present on the antennae of the German cockroach. Such chemoreceptors are likely present on the antennae of other arthropods as well. It has also been determined that male cockroaches are generally more sensitive to odors than female cockroaches.

DETAILED DESCRIPTION

Figure 1:
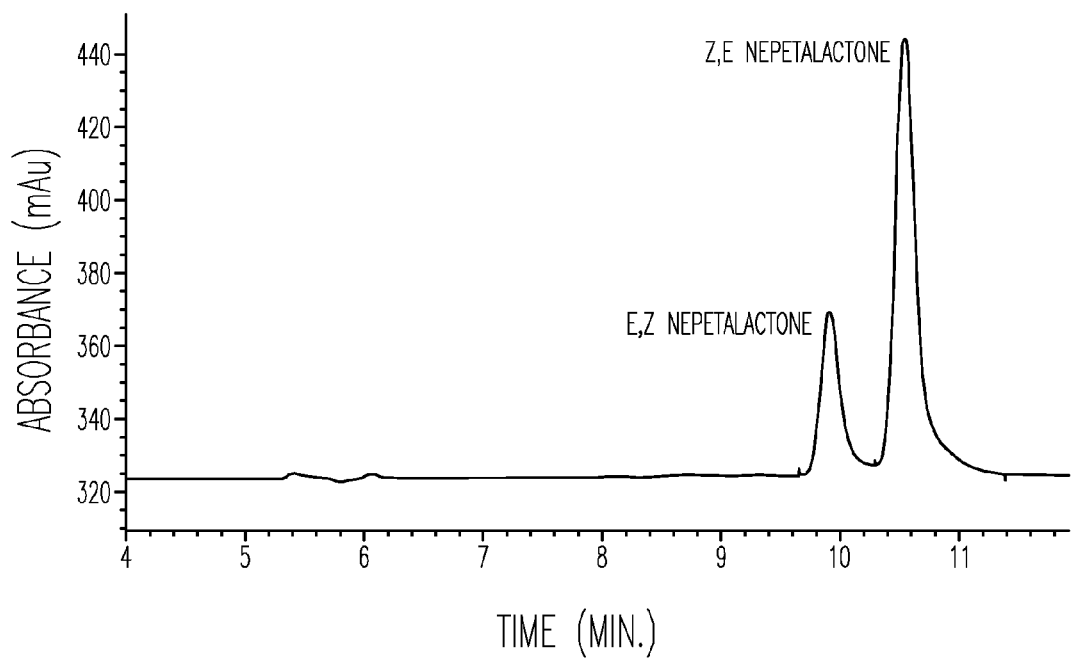
FIG. 1 shows a high performance liquid chromatograph ("HPLC") profile for the essential oil contained in a steam distillate of catnip in "absorbance" in milli-absorbance units (mAu) versus "time" in minutes (min), at a wavelength of approximately 254 nanometers (nm) in one embodiment of the present invention.

In the following detailed description of the preferred aspects, reference is made to the accompanying drawings, which form a part hereof, and in which is shown by way of illustration specific preferred aspects in which the invention may be practiced. These aspects are described in sufficient detail to enable those skilled in the art to practice the invention, and it is to be understood that other aspects may be utilized and that chemical, mechanical, procedural and other changes may be made without departing from the spirit and scope of the present invention. The following detailed description is, therefore, not to be taken in a limiting sense, and the scope of the present invention is defined only by the appended claims, along with the full scope of equivalents to which such claims are entitled.

Compositions useful in repellency against arthropods are disclosed. Various terms are defined first, followed by a description of the preferred sources of the monoterpenoids (e.g., catnip) and sesquiterpenoids (e.g., Osage orange, Amyris plant and Siam wood). The repellency of the various compositions made from these compounds is described next, followed by specific examples.

Definitions

The term "applying" as used herein includes any suitable method of emitting an effective repellent amount of a plant volatile compound in a target area. This includes broadcast or restricted localized spraying of a volatile, in or around an area, with or without first micro-encapsulating the volatile, emitting the volatile from one or more controlled-release point-source dispensers in or around an area, and integrating the release of the volatile with an irrigation technique (chemigation). "Applying" can also refer to emitting liquid or solid repellents through use of creams, liquid-based products, powders, and so forth.

The term "biorational" as used herein refers to a pest management agent that is natural or otherwise based on biological approaches, such as plant products, insect hormones, pheromones, and so forth, as opposed to synthetic chemicals not based on any biologically-known compounds, e.g., DEET. It includes not only "botanical" agents, i.e., agents derived directly from a plant source, but further includes analogs or derivates of those agents.

The term "carrier" as used herein refers to a component that, when combined with a repellent compound, produces a composition that can be delivered to a target pest as a repellent. A carrier can include, but is not limited to various liquids, solids and gases. This includes, but is not limited to, oils, including any type of vegetable oils, such as canola oil, soybean oil, and so forth, polymers, such as slow-release polymers, plastics, waxes, wood, gels, colloids (e.g., creams and lotions), granular materials, such as clays and minerals (e.g., vermiculite, bentonite), dusts, powders, sprays, drenching means, emulsifiable concentrates, and so forth. This can include products such as floor polish, silicone caulking, as well as misters or aerosol sprays, and so forth. The choice of carrier depends on several factors, including, but not limited to, the specific need, the size of the target area, and so forth.

As used herein, the term "controlled-release point-source dispenser" is one type of delivery means for a composition comprising the repellent compound and a carrier. Such a dispenser includes any suitable method for controlling the emission rate of the volatile compound from a concentrated source reservoir of the compounds. Such methods include, but are not limited to, pads, beads, rods, spirals, or balls comprised of rubber, leather, cotton, wood or wood products, polyethylene, polypropylene or polyvinyl chloride that are impregnated with the volatile compound; micro-capillary tubes open at one end; sealed polyethylene or polypropylene tubes sealed at both ends; laminates comprised of layers of the volatile compound alternated with plastic and cut in various sized flakes or preserved as large ribbons or sheets; permeable or semi-permeable membranes covering a non-permeable container serving as a reservoir for the volatile compounds; large porous beads or sponges; micro-capsules; sealed envelopes or bags made of polyethylene, polypropylene, paper, cardboard, or other permeable substances, metered aerosol systems utilizing pump or pressure technologies to emit aerosolized droplets of the volatiles into the atmosphere, onto plants surfaces or soil, or onto any of the above controlled-release point-source dispensers; and non-aerosol micropump technologies that cause metered quantities of the compounds to be dispensed and volatilized by any of the above methods.

The term "essential" as used herein in the phrase "essential oil" refers to the "essence" or "smell" of the oil that is distinctive to a particular plant, such as catnip or Osage orange. The "essential oil" of a plant contains the volatile components.

The term "fumigation" as used herein refers to the use of a gas repellent, or a volatile solid or liquid repellent to control pests in storage bins, buildings, ships, rail cars, stored products, organic materials such as soil, foods, animal feed, compost, and so forth, living organisms such as plants, or in any closed areas, i.e., target areas, which are prone to having pests, i.e., pest infestation.

The term "mature" or "ripe" as used herein typically refers to a fruit that has detached from a branch and fallen to the ground, although a "ripe" fruit in some instances may still be attached to the branch and within a few days of detaching. An "unripe" or "immature" fruit is necessarily a fruit that is still attached to a branch, but is not within a few days of detaching from the branch. In some instances, "maturity" can be defined by the calendar, such that fruit collected after a certain date is considered "ripe," whereas fruit collected prior to that date is typically "unripe." For example, fruit of the Osage orange which is collected after approximately September 30 in the Northern Hemisphere is generally considered to be "ripe," whereas fruit collected prior to that date in this hemisphere is typically in an "unripe" state. Obviously, the growing season can vary from year to year and at different latitudes. For example, in some years "ripe" Osage orange fruit may be present as early as mid-September, whereas, "unripe" Osage orange fruit may still be present in mid-October. With respect to many fruits, such as the Osage orange, it appears that the chemical make-up is different in a "ripe" fruit as compared with an "unripe" fruit. For example, preliminary tests indicate that "ripe" Osage oranges have a significant amount of hexyl hexanoate, i.e., in excess of about 30% of the volatile fraction whereas "unripe" fruit does not appear to have more than trace amounts of this compound.

The term "monoterpene" as used herein refers to a compound having a 10-carbon skeleton with non-linear branches. A monoterpene technically refers to a compound with two isoprene units connected in a head-to-end manner. The term "monoterpenoid" refers to a monoterpene-like substance and may be used loosely herein to refer collectively to monoterpenoid derivatives as well as monoterpenoid analogs. Monoterpenoids can therefore include monoterpenes, alcohols, ketones, aldehydes, esters, ethers, acids, hydrocarbons without an oxygen functional group, and so forth. It is common practice to refer to certain phenolic compounds, such as eugenol, thymol and carvacrol, as monoterpenoids because their function is essentially the same as a monoterpenoid. However, these compounds are not technically "monoterpenoids" (or "monoterpenes") because they are not synthesized by the same isoprene biosynthesis pathway, but rather by production of phenols from tyrosine. However, common practice will be followed herein.

As used herein, the term "repel" means that less time is spent in a given area, i.e., a target area, than in an available non-target or untreated area. "Repel" can also mean that no time is spent in the target area. As such, "repelling" a pest includes deterring a pest from remaining in a target area, as well as keeping a pest away from a target area. In some instances, a pest may be "slowed" in behavior and responsiveness after coming in contact with a repellent, such that the presence of the target pest is less of a nuisance to a human or animal in the target area. Slowing a target pest may also allow it to be killed by other means. The total number of pests in an area may be considered to be "suppressed" or even "eliminated" due to use of a "repelling agent" or a "repellent."

The term "sesquiterpene" as used herein refers to a compound having a 15-carbon skeleton with non-linear branches. The term "sesquiterpenoid" refers to a sesquiterpene-like substance and may be used loosely herein to refer collectively to sesquiterpenoid derivatives as well as sesquiterpenoid analogs. Sesquiterpenoids can include sesquiterpenes, alcohols, ketones, aldehydes, ethers, acids, hydrocarbons without an oxygen functional group, and so forth.

The term "suppress" as used herein means to reduce or limit the incidence or severity of a pest infestation or pest activity, even if for a limited period of time.

The term "target area" as used herein includes any place where the presence of target pests is not desirable, including any type of premises, which can be out-of-doors, such as in gardens, lawns, tents, camping bed nets, camping areas, and so forth, or indoors, such as in barns, garages, commercial buildings, homes, and so forth, or any area where pests are a problem, such as in shipping or storage containers (e.g., bags, boxes, crates, etc.), packing materials, bedding, and so forth. Target area can also include the outer covering of a living being, such as skin, fur, hair, or clothing.

The term "volatility" as used herein is defined as the property of a substance having a low boiling point and a high vapor pressure at ordinary temperatures and pressures. Similarly, the term "volatile" is considered to refer to a compound that is readily vaporizable at a relatively low temperature. A "slightly volatile" compound may be considered to have a vapor pressure of between about 0.05 Pascal (Pa) and two (2) Pa. Slightly volatile repellents can be considered to include DEET (vapor pressure of 0.22 Pa), as well as many of the preferred repellents of the present invention that contain nepetalactone, nepetalactone isomers or certain sesquiterpenoids. "Slight" volatility is a desirable property for a repellent because it provides an additional route of exposure against a target pest, i.e., fumigation. Furthermore, the same amount of such a repellent is effective over a larger target area as compared with a non-volatile repellent, which is limited to only a contact route of exposure. "High" volatility is generally considered an undesirable property for a repellent, because such repellents typically dissipate too rapidly to be effective, e.g., citronella. The essential oil of a plant is considered to include only "volatile" components. Similarly, the term "plant volatile" as used herein refers to a volatilizing compound from any part of a plant, including, but not limited to, a leaf, root, flower or flower bud, fruit, vegetable, stem, and so forth.

The term "long term repellency" as used herein refers to agents that demonstrate repellency in excess of two (2) hours. This is in contrast to known botanical repellents, many of which offer protection of less than 20 minutes. See, Fradin, et al, *Comparative Efficacy of Insect Repellents Against Mosquito Bites*, N. Engl. J. Med., Vol. 347, No. 1 (Jul. 4, 2002).

The term "spatial repellency" or "percent repellency" as used herein is a measure of repellency caused by the vapors of the repellent material. In experimental testing, it is expressed as the percentage of target pests that are positioned in an untreated half of a treatment chamber, i.e., the half farther away from treated filter paper, compared to the number that choose to sit in the treated half of the chamber, i.e., the half nearer treated filter paper. A repellent having a spatial repellency of 80% or over is considered highly effective. A repellent having a spatial repellency of between at least about 70% or greater is considered a very good spatial repellent. And a repellent having a spatial repellency of at least 50% up to about 70% is a good spatial repellent. Spatial repellency below 50% may not provide suitable protection in use and is generally not considered a good spatial repellent, although such levels are considered statistically significant.

The term "contact repellency" or "contact irritancy" as used herein is a measure of repellency caused by direct contact of the repellent material by a target pest. Contact repellency is expressed as avoidance frequency. Significance is indicated as a "P" value which refers to degree of significant difference between the number of target pests resting on the treated filter paper versus a control. Therefore, a material that is highly effective as a contact repellent/irritant produces a P value that is very small (e.g., <0.001 or <0.0001). A material that is not effective as a contact repellent/irritant would have a P value that is greater than 0.05.

The term "residual repellency" as used herein refers to the amount of time a target pest is repelled away from a treated surface as either a spatial or contact repellent.

Description of the Embodiments

The compounds useful in the present invention include volatile terpenoids and combinations of volatile terpenoids.

In one embodiment, the compounds can include highly volatile and/or slightly volatile compounds derived from plant volatiles. Such compounds include monoterpenoids (highly volatile) and sesquiterpenoids (slightly volatile). In one embodiment, the compounds are monoterpenoids known as nepetalactone, including two of the individual isomers of nepetalactone, namely the Z,E- and E,Z-isomers in combination with one or more sesquiterpenoids. In one embodiment, the compounds are sesquiterpenoids, such as the sesquiterpenoids listed in Tables 5-7, as well as *Amyris* essential oil (from the wood of the West Indian sandalwood tree), Siam wood essential oil, (i.e., *Fokienia*, Vietnamese pemou oil), including any of the individual compounds found in Vietnamese pemou oil as listed in Table 1 of Weyerstahl, et al., *Constituents of Vietnamese pemou oil—a reinvestigation, Flavour Fragr. J.*, 14, 409-410 (1999), including but not limited to the two primary constituents, (E)-nerolidol and fokienol). In one embodiment, the sesquiterpenoid is any oxygen-containing sesquiterpenoid. In one embodiment, the sesquiterpenoid is any cyclic sesquiterpenoid, although the invention is not so limited, as certain acyclic sesquiterepnoids, such as (E)-nerolidol, have been shown to exhibit repellent properties. Other specific preferred compounds include hedycaryol, elemene, elemol, alpha-cubebene, cadinene, and so forth.

These compounds, when combined with a suitable carrier or vehicle, can be used as an insect repellent in target areas that include people, pets, livestock, cupboards, containers, houses, yards, gardens and so forth. The repellents can be used against a variety of target pests including cockroaches, mosquitoes, black flies, house flies, gnats, stored grain pests (e.g., maize weevil, red flour beetle, saw-toothed grain beetle, Indian meal moth), clothes moths, ticks, mites, spiders, and other arthropod pests. Much of the testing described in the Examples was performed on female yellow fever mosquitoes (*Aedes aegypti*), or the Northern House Mosquito (*Culex pipiens*). Both are important as disease vectors and nuisance species. The northern house mosquito carries West Nile Virus, and the *Aedes aegypti* carries yellow fever. Other mosquitoes tested include the Western Encephalitis Mosquito, (*Culex tarsalis*) which is also known to carry the West Nile virus in the western United States, among other diseases. Yet other testing was performed on the German cockroach. Again, it is expected that the novel compositions of the present invention will be effective against a variety of arthropods.

In one embodiment, the novel compositions described herein exhibit repellency in excess of 20 minutes up to two hours. In one embodiment, the compositions exhibit long term repellency, i.e., in excess of two (2) hours. In one embodiment, the compositions exhibit repellency between about 2 and 6 hours. In one embodiment, repellency is at least six hours. This is in contrast to known botanical repellents, many of which offer protection of less than 20 minutes. See, Fradin, et al, *Comparative Efficacy of Insect Repellents Against Mosquito Bites*, N. Engl. J. Med., Vol. 347, No. 1 (Jul. 4, 2002).

In one embodiment, *Amyris* essential oil or the individual compounds isolated from the *Amyris* plant, namely eudesmol, including any isomers present, or elemol, are used in repellent compositions. Again, elemol is a sesquiterpenoid, and *Amyris* essential oil consists mostly of two sesquiterpenoids, namely elemol and eudesmol. Elemol and eudesmol are major components of Osage orange.

Elemol has the following structure:

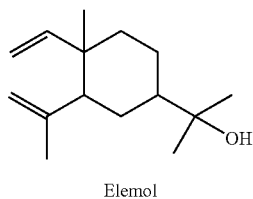

Elemol

Eudesmol has the following structure:

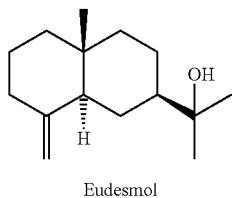

Eudesmol

Sesquiterpenoids are much less volatile and are not as effective as a spatial repellent as compared with catnip oil, for example. However, these compounds are effective contact repellents.

In one embodiment mixtures of monoterpenoids and sesquiterpenoids are used. Mixtures containing both catnip oil and various sesquiterpenoids have been shown to demonstrate both spatial and contact repellency. See Examples 7-10. However, it is likely that the individual isomers of catnip, i.e., E,Z-nepetelactone and Z,E-nepetelactone can also be combined with any number of sesquiternpoids to produce an effective long term repellent. In one embodiment, elemol is blended with a monoterpenoid, such as catnip essential oil and/or one or both of the individual isomers and a carrier for use as a repellent.

In one embodiment Siam wood essential oil or any of the components in Siam wood essential oil are used as repellents. In one embodiment, (E)-nerolidol, an acyclic sesquiterpene found in Siam wood essential oil is used. In another embodiment, fokienol, a cyclic sesquiterpenoid found in Siam wood essential oil is used.

In yet other embodiments, components such as p-menthane diol, cinnamic alcohol, wintergreen and/or citronella are used in combination with one or more sesquiterpenoids.

Various terpenoid compounds are isolated and purified from any source by any suitable method. In one embodiment, biorational sources, such as plants, fruits, and so forth, are used. In a particular embodiment, catnip (*Nepeta cataria*) is used as the source of nepetalactone, although the invention is not so limited. Nepetalactone is chemically related to certain cyclopentanoid monoterpenes isolated from insects, many of which are components of defensive secretions. (Eisner, T., 1964, *Science.* 146:1318). In a particular embodiment, two of the isomers of nepetalactone, namely cis-trans nepetalactone ("Z,E-isomer" or "Z,E-nepetalactone") and trans-cis nepetalactone ("E,Z-isomer or "E,Z-nepetalactone"), can each be used individually as the active compound in a repellent composition. In one embodiment, these isomers are also isolated and purified from the essential oil of catnip which is known to contain the monoterpene-derived iridodial compound nepetalactone (5,6,7,7α-tetrahydro-4,7-dimethylcyclopenta[e]pyran-1-(4αH)-one) (McElvain et al, 1941, *J. Am. Chem. Soc.* 63:1558-1563). It may be that these and other isomers, such as the Z,Z-isomer or E,E-isomer may be derived from other plants sources, such as *Nepeta mussini, Nepeta grandiflora* and *Nepeta nuda*. Such plant sources may also be used as an alternate source for nepetalactone. (See Eisenbraun, et al., 1980, *J. Am. Chem. Soc.* 45, 3811-3814).

Sesquiterpenoids are also useful as repellents and can be found in any number of biorational sources. In one embodiment, the fruit of the Osage orange tree (sometimes referred to as "hedge apple") is used as the source of the sesquiterpenoids. Other sources include, for example, *Ocimum micranthum* (Peruvian basil), which is known to contain γ-elemene isomers, β-elemene isomers, γ-copaene and β-selinene (Charles et al., 1990, J. Agric. Food Chem. 38(1): 120-122). The aromatic grass *Bothriochloa pertusa* is known to contain α-selinene, τ-cadinene, δ-cadinene and elemol (Kaul and Vats, 1998, Biochem. Syst. Ecol. 26: 347-356). Mangoes contain δ-cubebene, β-elemene, δ-selinene and γ-cadinene following enzymatic maceration (Sakho et al., 1998, J. Food Sci. 63(6): 975-978). Several compounds have been isolated from navel oranges, including β-copaene, δ-cadinene and hexyl hexanoate. Cubebene has been identified as a minor component of the shrub *Cleome monophylla* extracts. Sesquiterpenoids possessing the cubebene/copaene, elemene, selinene and cadinene skeletons were identified from antimicrobial extracts of *Leptospermum scoparium* and *Kunzea ericoides* (Porter and Wilkins, 1998, Photochemistry 50: 407-415). Yet other sources of sesquiterpenoids include Siam wood and the *Amyris* plant.

The isolated terpenoid can be of any suitable purity, such as 55% or more. In one embodiment, the purity is at least about 90%. In another embodiment, the purity is greater than 90%. In yet another embodiment, the purity is in excess of 99%.

Different formulations or routes of exposure can provide for even further uses. For example, in addition to exposing the target pest to the repellent by contact, and possibly aquatic exposure, any of these novel repellents can also be used as fumigants. Useful amounts to evoke repellency ("repellent" amounts) will depend on the particular application technique used and on the specific conditions in the area at the time of application. Such amounts can readily be determined by those skilled in the art. The determination by Applicants of the means of sensory input for the German cockroach, and likely other target pests as well, i.e., via antennae, will also aid in determining proper amounts for various applications.

In the examples described herein, nepetalactone was isolated from catnip by subjecting the leaves and stems to steam distillation. Nepetalactone purity in excess of 99% was achieved with this method. The resulting extract was tested for repellency against male German cockroaches (*Blattella germanica*) in a "choice" test arena, i.e., via contact. The two isomers of nepetalactone were also isolated, purified by preparative thin-layer chromatography (TLC), and tested for repellency in the same manner. Purity in excess of 97% was achieved for the Z,E-isomer and in excess of 91% for E,Z-isomer. (Nuclear magnetic resonance (NMR) testing can also be used for additional verification with isomers having even higher purity, i.e., about 99% or more). The nepetalactone isomers have the following structures:

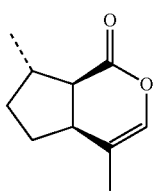 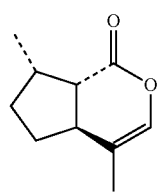

Z,E-nepetalactone      E,Z-nepetalactone

Significant differences due to concentration were detected using Analysis of Variance (ANOVA), a statistical method known in the art for finding significant differences between treatment types by analyzing variance between observations. Responses were compared using the well-known least-squared means analysis method. The minor isomer, E,Z-nepetalactone, appears to be significantly more repellent than the predominant isomer, Z,E-nepetalactone. Furthermore, at the lowest concentrations tested, the E,Z-isomer appears to be far more repellent to cockroaches than DEET, the primary known commercial standard insect repellent. It should be noted that known cockroach "insecticides" include various organophosphates, carbamates and pyrethroids. However, DEET and naphthalene have been used herein as the standards for comparison against the cockroach because there is no known cockroach "repellent" commercially available. (See Example 1).

The mature and immature fruits of the Osage orange (*Maclura pomifera*, family Moraceae) were extracted using several methods, including steam distillation, solid-phase micro-extraction (SPME), solvent extraction with hexane and Soxhlet extraction with hexane or methylene chloride. Each of these techniques resulted in an essential oil containing a number of sesquiterpenoids and other components. The extracts were subjected to gas chromatography and mass spectroscopy (GC-MS) to identify extract components. Ripe and unripe fruits were also compared using solid-phase micro-extraction (SPME). In addition to testing the essential oil of the Osage orange against the cockroach in a "choice" test arena, three of the identified components in the essential oil have also been similarly tested for repellency, namely elemol, alpha-cubebene and hexyl hexanoate (a non-sesquiterpenoid).

Siam wood can be extracted by any methods known in the art, including the methods described in Weyerstahl, et al., supra.

*Amyris* essential oil can also be extracted from the *Amyris* plant by any known method, including steam distillation or hexane extraction. In one embodiment, two isoflavanoids (which are non-sesquiterpenoids) are found in Osage orange, but not in the essential oil, namely, osajin and pomiferin are used in combination with a monoterpenoid or in combination with a monoterpenoid/sesquiterpenoid mixture.

Results to date indicate that the sesquiterpenoid components in the Osage orange as well as in the *Amyris* plant and Siam wood have excellent repellency against pests as compared with the non-sesquiterpenoids. Osajin, a non-sesquiterpenoid, did demonstrate repellency, but since it has no volatility, it can only be used as a contact repellent. The sesquiterpenoids also appear to have better efficacy than naphthalene, another commercial standard insect repellent (commonly used in moth balls). It is believed that several of the other sesquiterpenoids present in the essential oil of Osage orange as well as the Siam wood and *Amyris* plant (or combinations thereof) will also demonstrate similar or perhaps even better repellency properties. (See Example 2).

Preliminary tests with two species of mosquito, namely *Aedes aegypti* and *Culex tarsalis*, determined lethal levels of both the monoterpenoid and sesquiterpenoid compositions. (Example 5).

The series of experiments shown in Example 6 give supporting evidence for catnip and Osage orange essential oils, elemol, and nepetalactone as effective insect repellents to common household pests and pests of human health. Investigations with mosquito behavioral responses in a static-air apparatus showed that catnip essential oil, and elemol can act as effective mosquito repellents from treated surfaces, but differ in residual efficacy. Further studies are currently underway to evaluate residual repellency effects of other natural products in Osage orange essential oil and examine differences in the mechanism of repellency.

Specifically, comparisons of contact irritancy with German cockroach (*Blattella germanica*), and the house fly (*Musca domestica*) to catnip essential oil, and its major components, Z,E-nepetalactone and E,Z-nepetalactone with the commercial standard, N,N-diethyl-m-toluamide (DEET) are shown in Example 6. Both species showed high percentage repellency values when exposed to filter paper treated with catnip essential oil or the individual nepetalactone isomers. Of the two nepetalactone isomers evaluated, German cockroaches were most responsive to the E,Z isomer. House flies showed similar trends in contact irritancy, responding to surfaces treated with the predominant catnip isomer, Z,E-nepetalactone, more intensely than to the catnip essential oil. These results are also shown in Example 6.

Two mosquito bioassays were used to measure percentage and contact repellecy. Mosquitoes responded initially with high percentage repellency to surfaces treated with catnip essential oil. From the residual repellency study, this trend in repellency by the catnip oil significantly decreased over the 180-minute test period. Elemol and DEET initially had lower percentage repellency values than catnip essential oil, but did not show the negative relationship between percentage repellency and time, retaining excellent repellency throughout the 3-hour bioassay. Solutions with elemol and DEET exhibited greater significance in contact repellency compared to catnip essential oil. These results show that catnip essential oil is a potent mosquito repellent, but does not provide the same residual effects as the commercial standard, DEET. Elemol, a sesquiterpene extracted from the fruit of the Osage orange, shows excellent promise as a mosquito repellent with comparable activity to DEET in contact and residual repellency. These results are also shown in Example 6.

Various other sesquiterpenoids and sesquiterpenoid/monoterpenoid blends have also been tested as discussed above (Examples 7-10). As noted above, catnip essential oil is mostly made up of the geometric isomers of monoterpenoid nepetalactone both of which volatilize easily. As a result, catnip essential oil is not an effective contact repellent although it is a very potent spatial repellent.

Results of testing with sesquiterpenoids derived from Siam wood and the *Amyris* plant, have shown that these compounds are also useful as repellents herein, either alone or in combination with the monoterpenoid, catnip essential oil. See Examples 7-10.

An experiment was also conducted to determine how arthropods detect repellents. It is known that DEET is effective as a repellent against mosquitoes because it can mask the odor of lactic acid, likely by interacting with a lactic acid receptor in the antennae of the mosquito. (E. Davis et al., 1976, *J. Comp.* Physiol. 150, 43-54). However, it is not known how other repellents are detected by mosquitoes, nor is it known how pests other than mosquitoes detect any type of repellent. In order to determine whether the antenna plays a role in repellent detection for arthropods other than mosquitoes, the experiment involved removing the antennae of several German cockroaches. The antennectomized cockroaches were exposed to concentrations of repellents that were shown to be active in the previous experiment. In all cases, the cockroaches were indifferent to the repellents, spending a nearly equal time on each piece of filter paper, i.e., treated and untreated. Since these cockroaches had never before encountered these repellents, the response was not considered to be learned or conditioned behavior. This experiment conclusively demonstrates that cockroaches, and likely most other arthropods having antennae, detect repellents with their antennae. (See Example 3). Differences between male and female cockroaches were also evaluated. It was confirmed that male cockroaches are more sensitive to odors than females. Female cockroaches were indifferent to DEET at concentrations that produced a definitive response in males. The females were also less strongly repelled by the Osage orange extract than the males. (See Example 4).

The invention will be further described by reference to the following examples, which are offered to further illustrate various embodiments of the present invention. It should be understood, however, that many variations and modifications may be made while remaining within the scope of the present invention.

Example 1

Insects. German cockroaches (*Blattella germanica*) were obtained from a colony at the Entomology Department of Iowa State University, Ames, Iowa. This colony was established several years ago by trapping wild cockroaches. The cockroaches have been kept in a 20-gal fish aquarium having approximately the top five (5) cm lined with "Insect Trap Coating" made by the Tanglefoot Company having offices in Grand Rapids, Mich. The next five (5) cm is lined with conventional petroleum jelly to help prevent the cockroaches from entering the coating, where they will die. The aquarium is covered with a piece of plexiglass having about a 7.5 cm (three (3) in) hole into which a screen has been placed. Small cardboard shelters are also kept in the aquarium to provide a place for the cockroaches to hide. A water bottle stopped with a dental wick is kept in the aquarium along with any conventional type of dry cat food in the cage bottom. Typically about ½ cup of dry cat food is kept in the cage. The cockroaches present in the aquarium are typically a combination of recently-trapped cockroaches and the existing colony of cockroaches. Additional cat food, such as about ¼ cup once a week, is added to the aquarium. Old cat food is removed and replaced periodically, particularly if it develops mold. Fresh water is also added to the water bottle periodically. The water bottle is replaced if mold develops on the wick. Approximately every four (4) to six (6) months, the colony is transferred to a clean aquarium.

Standard and Comparison Compounds. DEET was purchased from Aldrich Chemicals having offices in Milwaukee, Wis. Acetone and hexane, each having a purity in excess of 99% were purchased from Fischer Scientific Inc. having offices in Pittsburgh, Pa.

Starting Materials. Fresh catnip at various flowering stages was collected from unsprayed wild areas of the Iowa State University campus in Ames, Iowa as needed during the growing season. Plants not distilled immediately were frozen at −80° C. until needed for steam distillation. In some instances, frozen plants were used in conjunction with fresh catnip. The leaves and stems were either crushed while still frozen or otherwise cut up into small pieces while still fresh, in preparation for steam distillation. The crushed or cut-up leaves and stems were then placed into a five (5)-liter three-necked boiling flask and steam distilled according to the method of Pavia, et al., 1988, *Introduction to Organic Laboratory Techniques*, 3rd edition, Harcourt Brace College Publishers, Fort Worth, Tx. The collected distillate was washed two times with one (1) volume each of hexane in a separatory funnel to remove the oil layer from the water layer. The hexane was removed using rotary evaporation vacuum distillation at 500 mm Hg vacuum and 25° C.

A portion of the liquid obtained from rotary evaporation was diluted to about one (1) µl/ml with hexane and subjected to chromatographic analysis. Identification of the components was obtained using a Varian Gas Chromatograph, series 3700, made by Varian Inc., having offices in Palo Alto, Calif., with a two-meter packed 3% OV 101 column, nitrogen carrier, FID-detector, injector temperature of 250° C., an injection volume of 1.5 µl, with an initial column temperature of 70° C., ramped at 5° C./min to 150° C. and held for 8 minutes. The Z,E-isomer had a retention time of about 10.75 min, and the E,Z-isomer had a retention time of about 11.25 min. The ratio of Z,E-isomer to E,Z-isomer was about 6:1, as determined by calculating the areas under the peaks. These isomers together comprised over 98% of the steam distillate. Minor components were not identified.

HPLC was conducted using a Hewlett Packard series 1100 HPLC made by Hewlett Packard Inc. having offices in xx city, xx state, with a Pirkle Covalent Phenylglycine hi-chrom preparative column (25 cm×10 mm I.D., 5 microns S5NH Modified Spherosorb), having an injection volume of 25 µl, a mobile phase of 9:1 hexane:ethyl acetate at about 2.5 ml/min flow rate, and detection using a Spectroflow 757 UV-Detector at 254 nm.

The two isomers of nepetalactone were separated using silica gel preparative TLC plates (Whatman 20×20 cm, thickness: 1000 µm) with a solvent system of approximately 19:1 hexane:ethyl ether. The plates were run seven (7) times, allowing them to dry completely between each run. The resulting bands, which included a "wide" band and a "thin" band, were each illuminated under 254 nm UV-light. The silica gel was then scraped off the plates and washed with three washings of ether. The resulting solution was filtered and the ether solvent was removed by rotary evaporation. Purity was assessed using HPLC.

Figure 2:
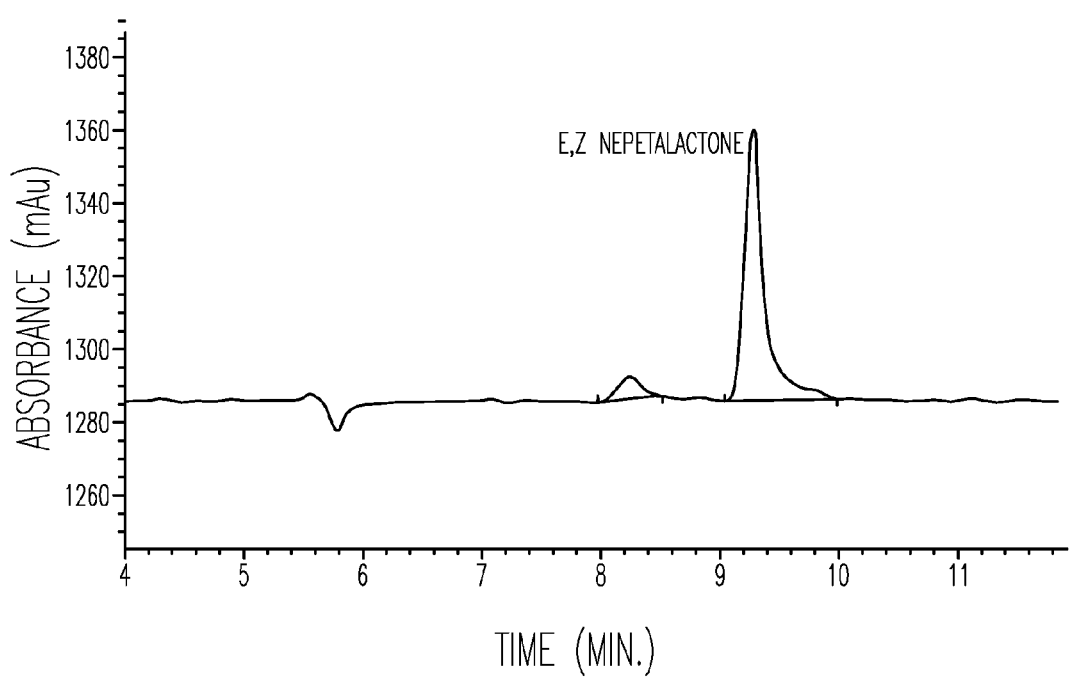
FIG. 2 shows an HPLC profile for E,Z-nepetalactone isolated from the steam distillate described in FIG. 1 in absorbance (mAu) versus time (min), at a wavelength of approximately 254 nanometers (nm) in one embodiment of the present invention.
Figure 3:
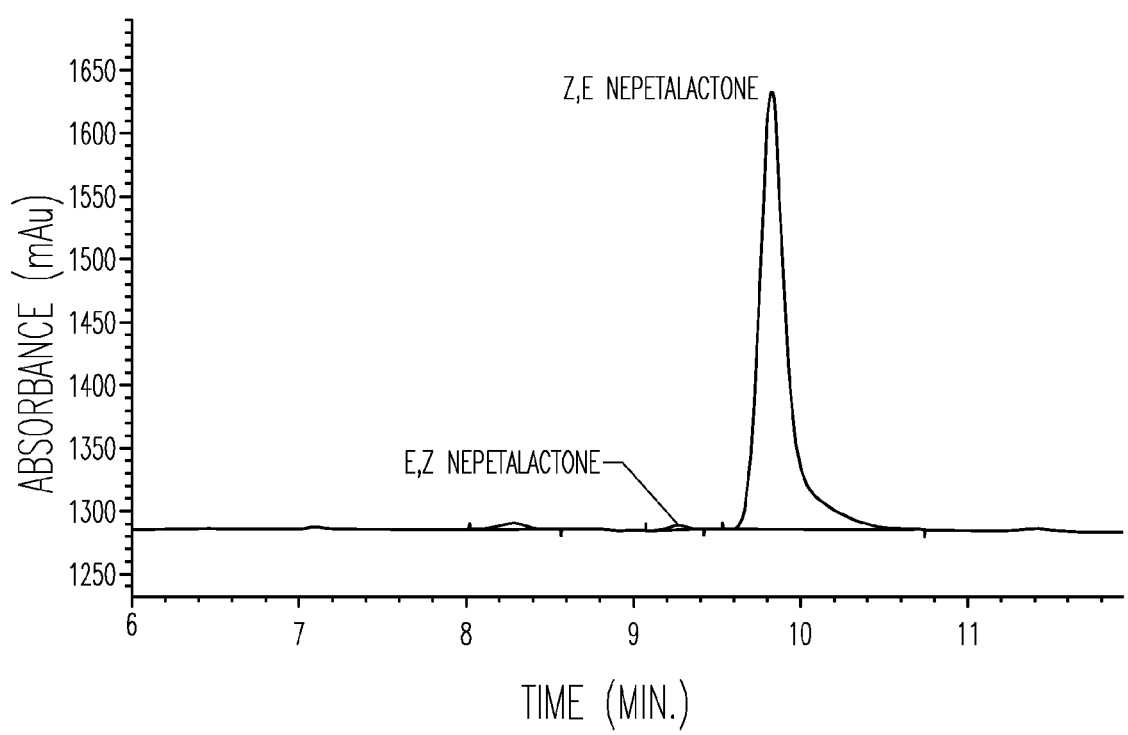
FIG. 3 shows an HPLC profile for Z,E-nepetalactone isolated from the steam distillate described in FIG. 1 in absorbance (mAu) versus time (min), at a wavelength of approximately 254 nanometers (nm) in one embodiment of the present invention.

Retention times and area percentage for the steam distillate and the two isomers are shown in Table 1 and FIGS. 1 through 3.

TABLE 1

HPLC Results for Catnip Steam Distillate, E,Z-Isomer and Z,E-Isomer

|  | E,Z-isomer | Z,E-isomer |
| --- | --- | --- |
| (FIG. 2) Catnip steam distillate retention time (minutes) | 9.9 | 10.5 |
| area % | 25.2 | 74.8 |
| (FIG. 3) "wide" band on TLC retention time (minutes) | — | 9.3 |
| area % | — | 91.3 |
| (FIG. 4) "thin" band on TLC retention time (minutes) | 9.8 | — |
| area % | 97.5 | — |

As Table 1 shows, the wide band on the TLC plate consisted predominantly of the Z,E-isomer, and the thin band was determined to consist mostly of the E,Z-isomer. On HPLC, as shown in FIG. 1, the second peak represents the Z,E-isomer, and the first peak is the E,Z-isomer. Comparing the areas for each band, the HPLC graphs show that the TLC procedure was accurate and efficient in separating the two isomers. FIG. 1 indicates a purity of the steam distillate in excess of about 99%, with about 25.2% of E,Z-isomer present and about 74.8% of the Z,E-isomer present. FIG. 2 indicates a purity of the E,Z-isomer of at least about 91.3%. The remaining components are unknown at this time. Similarly, FIG. 3 shows that the Z,E-isomer can be isolated at a purity of at least about 97.5%, with the remaining components being about 0.8% of the E,Z isomer and about 1.7% unknowns.

Gas-chromatography/mass spectroscopy of the nepetalactone isomers was also conducted on a Varian 3400 gas chromatograph, with a DB-5 ms nonpolar 30-m column (0.25 mm ID, 0.25 mm film thickness). The gas chromatography was coupled to a Finnigan TSQ 700 triple quadrupole mass spectrometer (San Jose, Calif.), electron impact of 70 eV. The mass spectral analysis of the isomers revealed that the two compounds are nearly indistinguishable by mass spectrometry, as is expected with isomers. The Z,E-isomer eluted off the column at 2.26 minutes, showing ions at m/z 166 [M$^+$] (100%), m/z 123 (78.5%), m/z 109 (46.3%), m/z 95 (58.8%), m/z 81 (62.2%) and m/z 69 (46.7%). The E,Z-isomer eluted off the column at 2.67 with the following mass spectrum: m/z 166 [M$^{+1}$] (100%), m/z 166 (99.9%), m/z 109 (51.8%), m/z 95 (66.6%), m/z 81 (67.0%) and m/z 69 (50.2%). Since both peaks have essentially identical mass spectra, these results are a further indication that the compound is nepetalactone, even though it contains two different isomers.

Test Procedure. Repellency bioassays were conducted to assess the repellent properties of compositions containing catnip steam distillate (nepetalactone), Z,E-nepetalactone, E,Z-nepetalactone and DEET against cockroaches. Certified acetone and certified hexane were also tested in order to evaluate solvent effects. (DEET was dissolved in acetone, because DEET is insoluble in hexane. The tested compounds were dissolved in hexane because hexane was the solvent used to extract these compounds from the distillate).

One Whatman 125-mm round filter paper was cut in half. One side was treated with one (1) ml of the test compound and the other side was treated with one (1) ml of solvent. The papers were allowed to dry in a fume hood for approximately two (2) minutes before being placed in a 150-mm Petri dish arena. The relative position of the treated side (i.e., to the right or left) of the dish was randomized using a random number table. The top of the Petri dish had a hole cut into the center for introduction of one cockroach at a time directly into the center of the arena. The hole was stopped using a small piece of tape to prevent the insect from escaping. One adult male German cockroach (*Blattella germanica*) was selected from the colony and dropped into the pre-formed hole in the Petri dish lid. Immediately after introduction of the cockroach, the number of seconds the cockroach spent on the treated or untreated side during a 300-second (five (5) minute) period was recorded with two different (2) stopwatches. Ten (10) replications were performed for each test compound.

Results. Using mean values and their related Standard Error of the Mean values (SEM), repellency of the selected samples was determined as shown in Table 2. Significance due to concentration was determined using ANOVA. Means for each dose were compared using the least squared means analysis on SAS (SAS Institute 1991) as shown in Table 3. Table 3 also shows a percent repellency for each test performed. Comparisons between test compounds were made using a two-tailed paired t-test ("paired t-test") which indicates "differences" as is known in the art and shown in Table 4 (as compared with a "one-tailed" test, which indicates "greater or less than").

TABLE 2

Nepetalactone and Nepetalactone Isomer Repellency Against the German Cockroach as Compared with DEET, Acetone and Hexane

| Controls | Treated vs Untreated | Results of 300-second tests | | | |
|---|---|---|---|---|---|
| | | Mean Treated (seconds) | SEM | Mean Untreated (seconds) | SEM |
| | Acetone vs Acetone | 143 | 11.2 | 159 | 11.3 |
| | Hexane vs Hexane | 147 | 5.6 | 155 | 5.5 |
| DEET | 10% vs Acetone | 63.4 | 15.9 | 238 | 15.6 |
| | 5% vs Acetone | 113 | 14.5 | 190 | 14.1 |
| | 1% vs Acetone | 120 | 13.8 | 181 | 13.8 |
| | 0.5% vs Acetone | 128 | 9.7 | 175 | 9.6 |
| | 0.1% vs Acetone | 129 | 9 | 175 | 8.8 |

TABLE 2-continued

Nepetalactone and Nepetalactone Isomer Repellency Against the German Cockroach as Compared with DEET, Acetone and Hexane

| Controls | Treated vs Untreated | Results of 300-second tests | | | |
|---|---|---|---|---|---|
| | | Mean Treated (seconds) | SEM | Mean Untreated (seconds) | SEM |
| Nepetalactone (Steam distillate) | 5% vs Hexane | 68 | 14.7 | 235 | 14.7 |
| | 1% vs Hexane | 109 | 19.6 | 192 | 19.8 |
| | 0.5% vs Hexane | 105 | 23.6 | 206 | 24.5 |
| Z,E-isomer | 5% vs Hexane | 47.3 | 8.7 | 252 | 8.4 |
| | 1% vs Hexane | 65.4 | 11.8 | 236 | 11.5 |
| | 0.5% vs Hexane | 128 | 10.4 | 174 | 10.3 |
| | 0.1% vs Hexane | 127 | 11.2 | 176 | 11.2 |
| E,Z-isomer | 0.5% vs Hexane | 31.7 | 5.2 | 270 | 5.3 |
| | 0.1% vs Hexane | 76.7 | 13.7 | 216 | 20.2 |

As Table 2 shows, control bioassays involving acetone and hexane showed no significant repellency. DEET at a level of ten (10) %, by volume, in the test solution was highly repellent. However, when comparing five (5) % DEET to five (5) % catnip (by volume) steam distillate, it can be seen that the catnip essential oil was a more effective repellent (as determined by the difference between the two mean values). Additionally, the one (1) % catnip steam distillate repelled cockroaches better than one (1) % DEET. At the 0.5% and 0.1% concentration levels, the E,Z-isomer repelled signifiantly better than the extract, DEET, and the Z,E-isomer (in descending order of comparative repellency).

The mean number of seconds spent by the cockroaches on the treated side of the arena, plus of minus the standard error of the mean (SEM) is reported in Table 3. The amount of test compound per unit area of filter paper is noted in "µg/cm$^2$" in Table 3. The percent by weight of each component listed in Table 2 can be converted to "µg/cm$^2$" by the following formula: (µg of compound/one (1) ml of solution)/area of filter paper in cm$^2$. For example, a solution containing "five (5) %", by volume, of a compound, is equivalent to a concentration of approximately "800 µg/cm$^2$" of that compound (e.g., five (5) % DEET is equivalent to a concentration of about 800 µg/cm$^2$ of DEET). Similarly, one (1) % DEET is equivalent to a conventration of approximately 160 µg/cm$^2$.

TABLE 3

Mean number of seconds (±SEM) spent on the treated side of the test arena by male *B. germanica* in 300 seconds

| Test Solution | Dose (µg/cm$^2$) | Mean seconds on treated side ± SEM | % repellency* |
|---|---|---|---|
| DEET | 1600 | 63.4 ± 15.9 b | 58 |
| | 800 | 113 ± 14.5 a | 26 |
| | 160 | 120 ± 13.8 a | 20 |
| | 80 | 128 ± 9.7 a | 16 |
| | 16 | 129 ± 9.0 a | 15 |
| | 0 | 143 ± 11.2 a | 5 |
| Catnip Essential Oil | 800 | 68.3 ± 14.7 b | 56 |
| | 160 | 109 ± 19.6 ab | 28 |
| | 80 | 105 ± 23.6 ab | 34 |
| | 0 | 147 ± 5.6 a | 3 |
| Z,E-Nepetalactone | 800 | 47.3 ± 8.7 b | 68 |
| | 160 | 65.4 ± 11.8 b | 57 |
| | 80 | 128 ± 10.4 a | 15 |
| | 16 | 127 ± 11.2 a | 16 |
| | 0 | 147 ± 5.6 a | 3 |

TABLE 3-continued

Mean number of seconds (±SEM) spent on the treated side of the test arena by male *B. germanica* in 300 seconds

| Test Solution | Dose (µg/cm$^2$) | Mean seconds on treated side ± SEM | % repellency* |
|---|---|---|---|
| E,Z-Nepetalactone | 80 | 31.7 ± 5.2 c | 79 |
| | 16 | 76.7 ± 13.7 b | 46 |
| | 0 | 147 ± 5.6 a | 3 |

For each test solution, means ± SEM followed by the same letter are not significantly different by least squared means analysis ($\alpha$ = 0.05).
*Percent repellency was calculated by the following formula: (untreated − treated/300) * 100

Significantly due to concentration was observed by two-tailed ANOVA for DEET (F=4.83, df=5, 54; P=0.001), Z,E-nepetalactone (F=20.00, df=4, 45; P=0.0001) and E,Z-nepetalactone (F=41.08, df=2, 27; P=0.0001). Significance due to concentration was not seen for the catnip essential oil at the 0.05 two-tailed significance level, but was seen at the 0.1 significance level (F=3.44, df=3, 36; P=0.0267). As shown in Table 3, all DEET concentrations tested below 1600 µg/cm$^2$ were not significantly different from the control by least squared means analysis ($\alpha$=0.05). However, catnip essential oil was significantly different from the control at a dose of 800 µg/cm$^2$. Furthermore, Z,E-nepetalactone was significantly different from the control at doses of 160 µg/cm$^2$ and higher. E,Z-Nepetalactone was also significantly different from the control at all doses tested, including the lowest tested dose of approximately 16 µg/cm$^2$.

Paired t-test coparisons ($\alpha$=0.05. df=9) between the different compounds at equilent doses were and shown below in Table 4.

TABLE 4

Paired t-test comparisons of equivalent doses of test compounds

| Dose (µg/cm$^2$) | Comparison | vs. | Calculated t-value |
|---|---|---|---|
| 800 | DEET | CNEO | 2.29* |
| | DEET | Z,E | 3.88* |
| | CNEO | Z,E | 1.75 |
| 160 | DEET | CNEO | 0.41 |
| | DEET | Z,E | 4.41* |
| | CNEO | Z,E | 1.91 |
| 80 | DEET | CNEO | 0.88 |
| | DEET | Z,E | 0.01 |
| | DEET | E,Z | 7.82* |
| | CNEO | Z,E | −0.88 |
| | CNEO | E,Z | 2.99* |
| | Z,E | E,Z | 7.87* |
| 16 | DEET | Z,E | 0.10 |
| | DEET | E,Z | 2.60* |
| | Z,E | E,Z | 2.50* |

*Difference is significant by two-tailed paired t-test at $\alpha$ = 0.05, df = 9.
CNEO = Catnip essential oil;
Z,E = Z,E-Nepetalactone;
E,Z = E,Z-Nepetalactone.

As Table 4 shows, catnip essential oil only differed from DEET at 800 µg/cm$^2$, and at lower doses. Z,E-Nepetalactone differed from equivalent doses if DEET above 80 µg/cm$^2$. However, E,Z-nepetalactone differed from DEET at all concentrations tested. Z,E-Nepetalactone, which comprises about 85% of the essential oil, did not differ from the catnip essential oil at any of the concentrations tested. E,Z-Nepetalactone was more active than the catnip essential oil at 80 µg/cm$^2$. Both Z,E- and E,Z-nepetalactone were compared at 80 and 16 µg/cm$^2$. It was found that E,Z-nepetalactone was significantly more active than the Z,E-isomer at both concentrations.

Conclusions. The crude steam distillate (nepetalactone) displayed "very good" repellency at every concentration tested, as is evidenced by the minimal amount of time the cockroach stayed on the treated side, as compared with the untreated side, i.e., approximately two (2) to three (3) times less. The individual isomers also demonstrated "very good" to "excellent" results. For example, the Z,E-isomer at five (5) % demonstrated "excellent" repellency, as the cockroach spent about five (5) times less time on the treated side as compared with the untreated side. The E,Z-isomer at 0.5% demonstrated "highly superior" repellency, as the cockroach spent about eight (8) times less time on the treated side as compared with the untreated side. It is quite likely that repellency would be high at other values as well. These compounds, in combination with a suitable carrier or delivery means have been demonstrated to be better than the commercial standard (DEET) for repellency against the German cockroach. Likely these compounds are also repellent against other arthropods as well.

Example 2

Insects. Cockroaches from the same source as described in Example 1 were used.

Standards and controls. Naphthalene having a purity in excess of 99% was obtained from Fischer Scientific Inc. The naphthalene, which was dissolved in acetone prior to testing, was used as a standard as this is one of the components in moth balls, a product used to repel clothes moths. (Again, there is no commercial standard for cockroach "repellents" per se, only for cockroach "insecticides"). Hexane having a purity in excess of 99% was also obtained from Fischer Scientific Inc.

Starting Materials. A series of GC-MS tests was undertaken to determine the various components of the Osage orange that could potentially be used as starting materials for repellency testing. The components were isolated using the methods described below, including steam distillation, Soxhlet extractions and hexane soaking (see Tables 5-6), as well as solid-phase micro-extractions (SPME) (see Table 7).

Some of the identified components were purified to at least about 95% and used in the repellency studies. Other identified components were purchased for use in these studies. All of these components were then dissolved in solvents prior to repellency testing. Specifically, osajin and pomiferin were purified to approximately 95% and 98%, respectively, and dissolved in acetone. Hexyl hexanoate and alpha-cubebene, having purities of 97% and 98%, respectively, were purchased from Fischer Scientific, Inc., and dissolved in hexane. Elemol, which was identified as a major component of the Osage orange, was also purchased and dissolved in hexane. Specifically, technical grade elemol (assayed at 55%), from Augustus Oils LTD, Borden, Hampshire, UK, was used because elemol at higher purity levels was not available at the time of testing.

Isolation Methods.

Steam distillation. The steam distillation method followed Pavia et al., 1988, *Introduction to Organic Laboratory Techniques*, 3d ed. Seven ripe fruits were ground by using a hand-powered meat grinder and placed in a 5000-ml three-necked round-bottom boiling flask. Water was added to cover the fruit pieces and boiled for approximately three (3) hours, i.e., until approximately 500-ml of condensate was collected. The collected water was washed twice with 250-ml hexane, and the water discarded. The hexane washings were passed through anhydrous sodium sulfate to remove water. The hexane washing was tested without further purification or concentration. The collected hexane extract was analyzed by gas chromatography and chromatography/mass spectrometry to identify mixture components.

Methylene Chloride and Hexane Soxhlet Extractions. One ripe fruit was cut into several pieces about two (2) cm$^3$ in size, and placed into two separate Soxhlets. One apparatus was charged with 500-ml methylene chloride and the other with 500-ml hexane. The Soxhlets were heated to the boiling point of the respective solvents and allowed to cycle for approximately 24 hours. Particulates were removed from the solution by vacuum filtration and the water was removed by filtration with anhydrous sodium sulfate. The collected extract was tested without further purification or concentration.

Chopped and Ground Hexane Soaking Extractions. One ripe fruit was cut into pieces about two (2) cm$^3$ in size and soaked for 24 hr in 500-ml hexane Another fruit was ground by using a hand-powered meat grinder and soaked for approximately 24 hr in 500-ml hexane. Particulates were removed from the extracts by vacuum filtration and the water was removed by filtration with anhydrous sodium sulfate.

Figure 4:
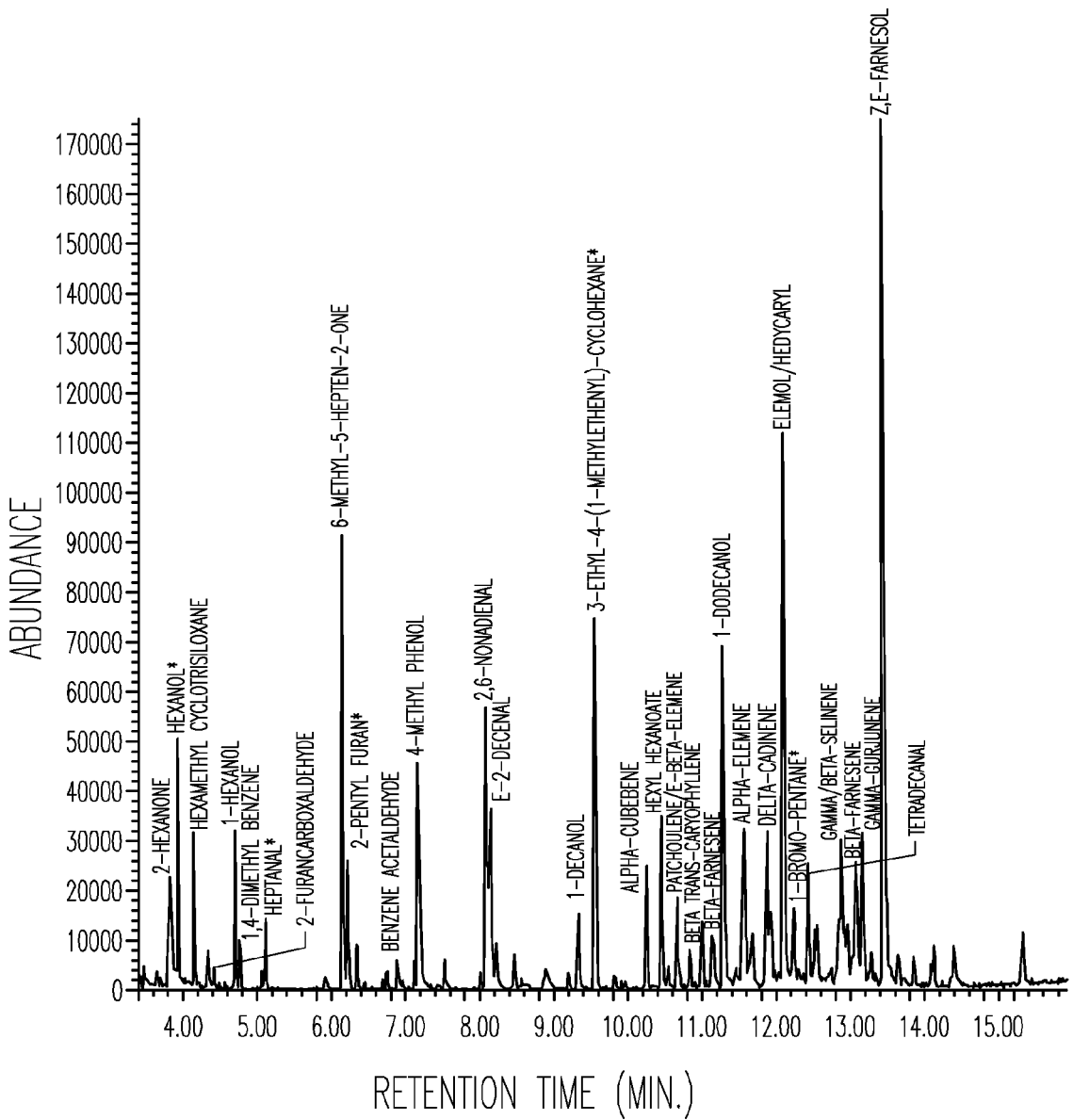
FIG. 4 shows a capillary gas chromatography ("GC") profile from volatiles collected from a steam distillate of a ripe Osage orange in abundance (of particles) versus retention time in minutes (min) in embodiments of the present invention. A labeled GC-peak indicates the volatile constituent was identified using mass spectrometry coupled with a GC retention time index.
Figure 5:
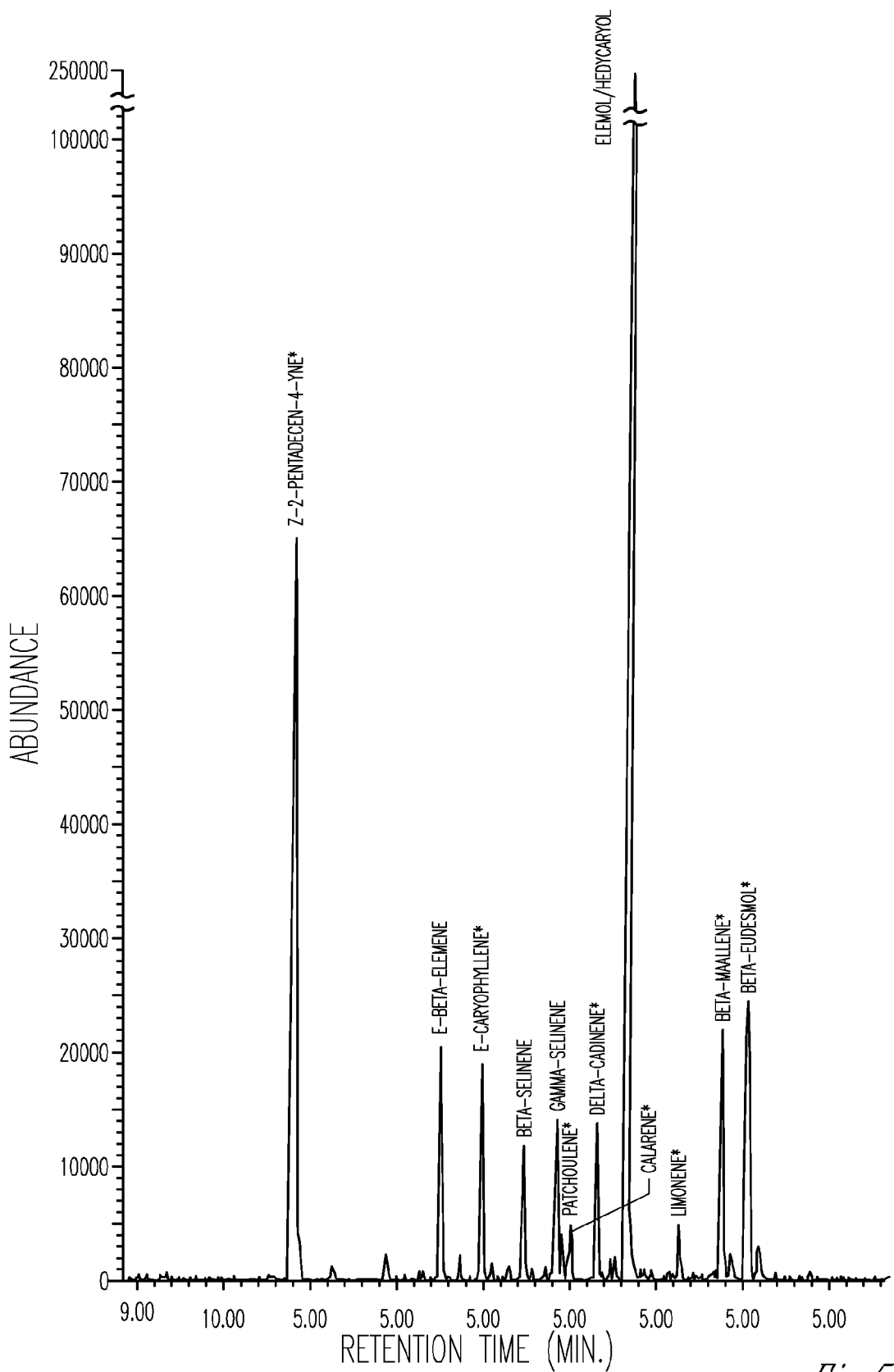
FIG. 5 shows a GC profile from volatiles collected from a steam distillate of an unripe Osage orange in abundance versus retention time (min) in embodiments of the present invention. A labeled GC-peak indicates the volatile constituent was identified using mass spectrometry coupled with a GC retention time index.

Table 5 shows the constituents identified by using the above-described isolation methods together with GC-MS for a ripe Osage orange. FIGS. 4 and 5 shows a profile of the constituents identified (using GC-MS) in the extract from the steam distillation isolation method for the ripe and unripe Osage orange, respectively, with some of the peaks labeled accordingly. "Approximate Percent Relative Area" refers to the area under the "peak" of a particular component, i.e., a percent of the total response by the detector during analysis. Such percentage is not directly equivalent to a specific volume or weight percentage of a particular component in the test solution. Actual concentrations of the various components can be determined by correlating these results with the area percentages of known standards by constructing a "standard curve," as is known in the art. In some instances, the approximate percent relative area is not reported, and the likely presence or non-presence of a component in a particular extract is noted with a "+" or "−."

Retention times and, in some instances, relative area percentage, for components in the ripe steam distillate, chopped hexane soak, ground hexane soak, methylene chloride Soxhlet and hexane Soxhlet extracts can be seen in Table 5. The retention times and abundance of the components in the ripe steam distillate of the Osage orange can be seen in FIG. 4. Generally, a component is listed below without qualification if the match quality was greater than 80%. Those components marked with an asterisk had a match quality of less than 80%. "Match quality" is a term known in the art that refers to the level of overlap with regard to a number of criteria (e.g., molecular weight, similarity of major fragment, etc.) between the compound being tested and a library of the spectra of known compounds stored in a database. The match qualities during mass spectroscopy of the various components listed in Table 5 varied considerably. Therefore, although it is possible that the components listed with low match qualities are correctly identified, further testing needs to be performed to verify these results with more certainty.

TABLE 5

Constituents of ripe Osage orange identified using steam and solvent extraction methods (Approximate Percent Relative Area)

| Retention time (min.) | Compound | Steam Distillate (Ripe) FIG. 4 | Chopped Hexane Soak | Ground Hexane Soak | MeCl$_2$ Soxhlet | Hexane Soxhlet |
|---|---|---|---|---|---|---|
| 3.84 | 2-Hexanone | 1.2 | + | − | − | − |
| 3.94 | Hexanal* | + | − | − | − | − |
| 4.15 | Hexamethyl cyclotrisiloxane | 1.4 | − | + | − | − |
| 4.33 | 2-Furancarboxaldehyde | 0.6 | − | − | − | − |
| 4.7 | 1-Hexanol | 1.1 | − | − | − | − |
| 4.76 | 1,4-Dimethyl benzene | 0.5 | − | − | − | − |
| 5.1 | Heptanal* | 0.5 | − | − | − | − |
| 6.13 | 6-Methyl-5-hepten-2-one | 3.8 | − | − | − | − |
| 6.2 | 2-Pentyl furan* | + | − | − | − | − |
| 6.87 | Benzene acetaldehyde | 0.5 | − | − | − | − |
| 7.16 | 4-Methyl phenol | 3.6 | − | + | − | − |
| 8.1 | 2,6-Nonadienal | 4.4 | − | − | − | − |
| 8.16 | E-2-Decenal | 2 | − | − | − | − |
| 9.34 | 1-Decanol | 0.9 | − | − | − | − |
| 9.57 | 3-Ethyl-4-(1-methylethenyl)-cyclohexane* | 5 | 1.1 | 2.5 | − | 1.2 |
| 10.26 | α-Cubebene | 1.7 | − | + | − | − |
| 10.47-10.5 | Hexyl hexanoate | + | 1.6 | 0.9 | − | − |
| 10.67 | Patchoulene/beta-Elemene | 1.2 | − | − | 0.4 | − |
| 11.01 | β-E-Caryophyllene | 0.9 | + | + | 0.2 | + |
| 11.17 | β-Farnesene | + | + | + | − | − |
| 11.3 | 1-Dodecanol | 4.8 | − | + | − | − |
| 11.58 | alpha-Elemene | 3.2 | − | 2 | − | − |
| 11.9 | δ-Cadinene | 2.5 | + | + | − | − |
| 12.13-16 | Elemol/Hedycaryol | 7.3 | 2 | 1.7 | 1.4 | 2.9 |
| 12.46 | 1-Bromo-pentane* | − | 0.8 | 1.6 | 0.5 | 0.6 |
| 12.56 | Tetradecanal | − | + | + | + | + |
| 12.89 | gamma/beta-Selinene | − | − | + | − | − |
| 13.09 | beta-Eudesmol | 3 | − | − | − | − |

TABLE 5-continued

Constituents of ripe Osage orange identified using steam and solvent extraction methods (Approximate Percent Relative Area)

| Retention time (min.) | Compound | Steam Distillate (Ripe) FIG. 4 | Chopped Hexane Soak | Ground Hexane Soak | MeCl$_2$ Soxhlet | Hexane Soxhlet |
|---|---|---|---|---|---|---|
| 13.17 | gamma-Gurjunene | 2.3 | − | + | − | − |
| 13.46-50 | Z,E-Farnesol | 13.6 | 3.8 | 9.4 | 1.7 | 1.6 |

*Match quality is less than 80%.
"+" Component is likely present in extract.
"−" Component is likely not present in extract.

Table 6 lists the components of the unripe steam distillate. The retention times and abundance of the components in the ripe steam distillate of the Osage orange can be seen in FIG. 5.

TABLE 6

Constituents of ripe Osage orange identified using steam and solvent (FIG. 5)

| Retention Time (min) | Compound |
|---|---|
| 10.76 | Z-2-Pentadecen-4-yne* |
| 12.48 | E-beta-Elemene |
| 12.95 | E-Caryophyllene* |
| 13.44 | beta-Selinene |
| 13.8 | gamma-Selinene |
| 13.83 | Patchoulene* |
| 13.95 | Calarene* |
| 14.30 | delta-Cadinene* |
| 14.65 | Elemol/Hedycaryol |
| 15.25 | Limonene* |
| 15.76 | beta-Maaliene* |
| 16.06 | beta-Eudesmol* |

*Match quality is less than 80%.

Solid-phase micro-extraction. To identify volatiles released from the Osage orange by other means, both ripe and unripe fruits were placed into separate one (1) liter glass containers. In this embodiment, head space volatiles were collected at room temperature by using a solid-phase micro-extraction (SPME) device, which contains a polymer fiber coated with approximately 100 _m of polydimethylsiloxane (Supelco Co., Bellefonte, Pa.). The SPME fiber was pre-conditioned for about two (2) hr at about 250° C. prior to volatile collection via exposure to the volatiles through a septum in the glass container. During the collection process, the fiber was exposed to and placed over the fruits in a glass container supplied with charcoal-filtered air at a flow rate of about 50 ml/minute. The collections continued for about 30 to 120 min, at which time the SPME fiber was immediately inserted into the injector of a GC-MC system for thermo-desorption. The GC-MS system was composed of a Hewlett Packard 5890 Series II gas chromatography equipped with a DB-5 column (30 m×0.25 mm inner diameter, J & W Scientific Co., Folsom, Calif.), and a Hewlett Packard 5972 Mass Selective Detector (MSD). The injector temperature was set at approximately 250° C. The split valve was opened approximately one (1) min after injection. The column temperature was initially about 40° C. for about one (1) min following the injection, then ramped to 250° C. at a rate of about 15° C./min. Mass spectra were recorded from 30 to 550 amu after electron impact ionization at 70 electron volts (eV).

Figure 6:
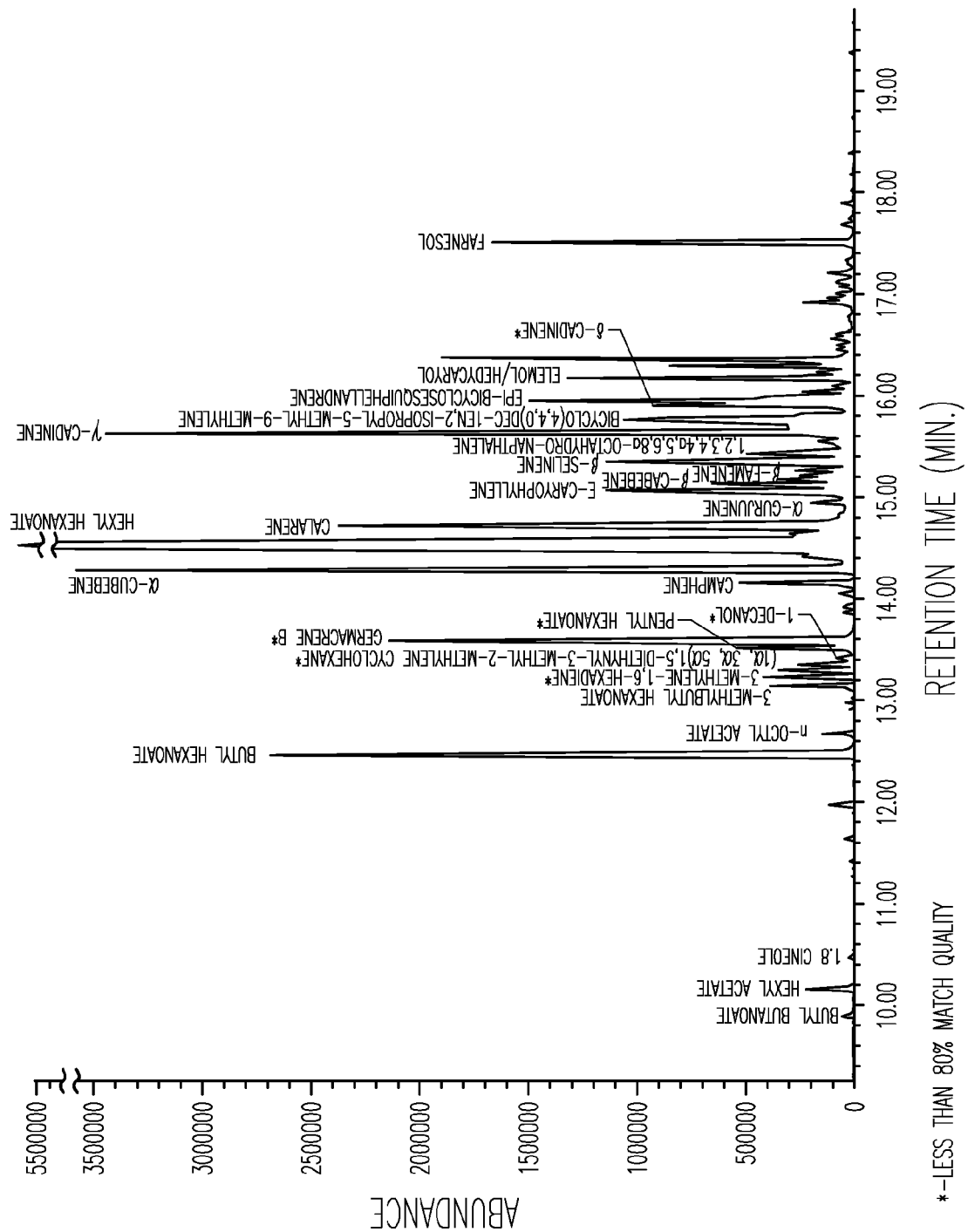
FIG. 6 shows a GC profile from volatiles collected from a solid-phase micro-extraction (SPME) of a ripe Osage orange in abundance versus retention time (min) in embodiments of the present invention. A labeled GC-peak indicates the volatile constituent was identified using mass spectrometry coupled with a GC retention time index.
Figure 7:
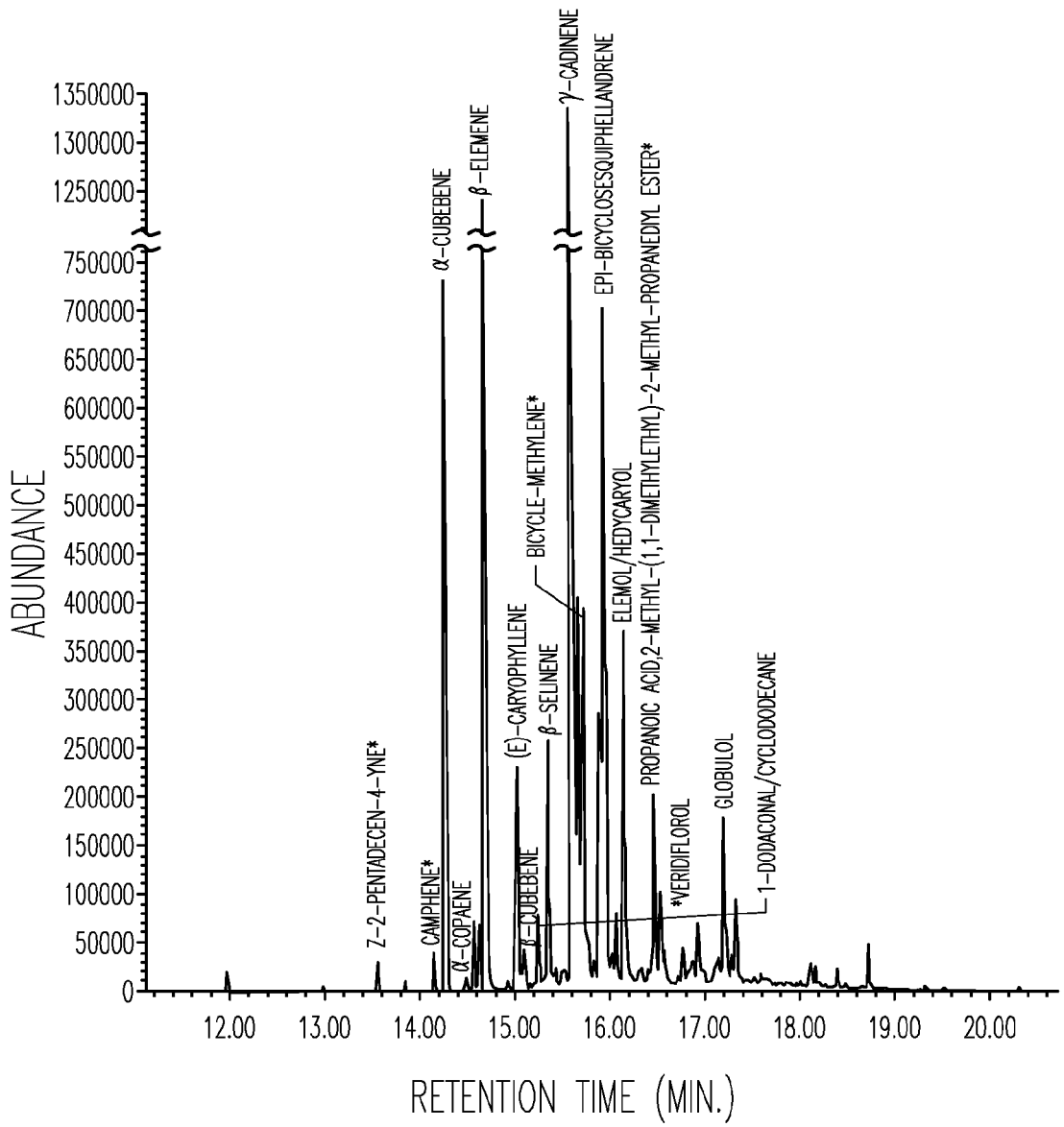
FIG. 7 shows a GC profile from volatiles collected from an SPME of an unripe Osage orange in abundance versus retention time (min) in embodiments of the present invention. A labeled GC-peak indicates the volatile constituent was identified using mass spectrometry coupled with a GC retention time index.

Table 7 and FIGS. 6 and 7 show the constituents identified in ripe and unripe Osage orange in the SPME extract (using GC-MS) with some of the peaks labeled in the profiles.

TABLE 7

Identification of volatile constituents in Osage orange using SPME and GCMS.

| Retention time (min.) | Compound | Unripe (cut) % Rel. Area | Unripe (intact) % Rel. Area FIG. 6 | Ripe (intact) % Rel. Area FIG. 7 |
|---|---|---|---|---|
| 9.9 | Butyl butanoate | − | − | 0.3 |
| 10.16 | Hexyl acetate | − | − | tr |
| 10.47 | 1,8-Cineole | − | − | tr |
| 12.48 | Butyl hexanoate | − | − | + |
| 12.68 | n-Octyl acetate | − | − | 0.3 |
| 13.15 | 3-Methyl butyl hexanoate | tr | − | 0.7 |
| 13.23 | 3-Methylene-1,6-hexadiene* | − | − | + |
| 13.3 | (1α, 3α, 5α)1,5-Diethynyl-3-methyl-2-methylene cyclohexane | − | − | + |
| 13.35 | 1-Decanol* | − | − | + |
| 13.52 | Pentyl hexanoate* | tr | − | 0.8 |
| 13.56 | Z-2-Pentadecen-4-yne* | − | + | − |
| 13.59 | Germacrene B* | − | + | + |
| 14.17 | Camphene* | 0.6 | 0.4 | 1 |
| 14.31 | α-Cubebene | 11 | 7.7 | 5 |
| 14.5-14.59 | Hexyl hexanoate | − | − | 30 |
| 14.56 | alpha-Copaene | + | − | − |
| 14.62-14.7 | β-Elemene | 17 | 14 | 4 |
| 14.74 | Calarene | − | − | + |
| 14.96 | α-Gurjuene | 0.2 | − | 0.3 |
| 15.07 | trans-Caryophyllene | 5.7 | 3.3 | 1.1 |
| 15.13 | β-Cubebene | − | + | 0.5 |

TABLE 7-continued

Identification of volatile constituents in Osage orange using SPME and GCMS.

| Retention time (min.) | Compound | Unripe (cut) % Rel. Area | Unripe (intact) % Rel. Area FIG. 6 | Ripe (intact) % Rel. Area FIG. 7 |
| --- | --- | --- | --- | --- |
| 15.22 | β-Farnesene | | – | + |
| 15.36 | 1-Dodecanol/Cyclododecane | | 3.3 | – |
| 15.38 | β-Selinene | 4.4 | 0.6 | 3 |
| 15.56 | 1,2,3,4,4a,5,6,8a-Octahydro-Naphthalene | tr | – | 0.5 |
| 15.66 | gamma-Cadinene | 17 | 23 | 6 |
| 15.75 | Bicyclo (4,4,0)dec-1-en, 2-isopropyl-5-methyl-9-methylene | 5 | 6 | 0.7 |
| 15.92 | δ-Cadinene* | – | – | 1.8 |
| 15.95 | EPI-Bicyclosesquiphellandrene | 3.8 | 7 | 2 |
| 16.18 | Elemol/Hedycaryol | 2.4 | 4 | 1.5 |
| 16.49 | Propanoic acid, 2-methyl-(1,1-dimethylethyl)-2-methyl-propanediyl ester* | | + | – |
| 16.55 | Veridiflorol* | tr | 0.9 | – |
| 17.22 | Globulol | | + | – |
| 17.52 | Farnesol | | – | + |

*Match quality is less than 80%
"+" Indicates that a component is likely present in an extract.
"–" Indicates that a component is likely not present in an extract.

The above results show that different types and amounts of various components are present in a mature or ripe Osage orange as compared with an unripe Osage orange. However, there are a number of other components in both the ripe and unripe Osage orange that have not yet been identified. Further work to identify these components and verify the identification of components currently having a low match quality, using a combination of these and other techniques known in the art, will eventually yield the complete make-up of both the ripe and unripe Osage orange.

Testing Procedure. The same procedure described in Example 1 was used.

Results. The results of this testing are shown below in Table 8.

TABLE 8

Osage orange essential oil and Osage orange individual component repellency against the German cockroach as compared with naphthalene

| | Amount Used | Mean Treated (Seconds) | SEM | Mean Untreated (Seconds | SEM | % repellency* |
| --- | --- | --- | --- | --- | --- | --- |
| Osage orange (unripe) (Steam Distillate) | 5 ml | 95.5 | 9.8 | 206 | 10.3 | 37 |
| | 1 ml | 78.3 | 12.6 | 223 | 12.2 | 48 |
| Osage orange (ripe) (Steam Distillate) | 1 ml | 64.8 | 20.2 | 235 | 20.2 | 57 |
| Ground Hexane Soak | 1 ml | 76.6 | 10.9 | 224 | 11 | 49 |
| Chopped Hexane Soak | 1 ml | 111 | 10 | 188 | 10.8 | 26 |
| Hexane Soxhlet | 1 ml | 85.5 | 13.6 | 208 | 13.1 | 42 |
| MeCl$_2$ Soxhlet | 1 ml | 116 | 10.5 | 184 | 10.3 | 23 |
| Osajin | 1% | 103 | 13 | 197 | 13.1 | 31 |
| | 0.5% | 117 | 11.6 | 184 | 12.2 | 22 |
| Pomiferin | 1% | 138 | 17.2 | 163 | 17.2 | 8.3 |
| Hexyl hexanoate | 1% | 142 | 5.9 | 158 | 5.7 | 5.2 |
| α-Cubebene | 0.5% | 99.4 | 14.6 | 211 | 15.9 | 36 |
| | 0.1% | 118 | 9.2 | 182 | 9.2 | 21 |
| Elemol (technical grade)~55% pure | 1% | 107 | 12.1 | 196 | 11.9 | 30 |
| Naphthalene | 1% | 117 | 14.8 | 184 | 14.6 | 22 |

*Percent repellency was calculated by the following formula: (untreated – treated/300) * 100

It should be noted that the concentration of essential oil for the unripe Osage orange steam distillate test solution was determined to be about 65 μg/one (1) ml. Specifically, through GC-MS, it was found that the concentration of elemol in the unripe steam distillate of the Osage orange was about 34 μg/ml. The percentage of elemol in the unripe steam distillate was determined to be approximately 52%. Because this 34 μg/ml was about 52% of the total unripe steam distillate, the concentration of the essential oil in the unripe steam distillate was estimated to be about 65 μg/ml. Because one (1) ml of the unripe steam distillate was applied to the filter paper in the assay, it is estimated that about 65 μg of essential oil was used in the apparatus. This indicates that the concentration of the essential oil on the filter paper was approximately 1.06 μg/cm$^2$.

As Table 8 shows, the sesquiterpenoids demonstrated repellency against the German cockroach. Specifically, alpha-cubebene demonstrated excellent repellency. Elemol also demonstrated very good repellency. However, it is known that the technical grade of elemol contains a significant amount of delta-codinene. Further repellency testing using a higher purity of elemol will likely yield different results.

Pomiferin and hexyl hexanoate are non-sesquiterpenoid components which performed relatively poorly, as the cockroaches appeared to be indifferent to these compounds at the concentrations tested. Osajin did demonstrate repellency against the German cockroach and may have some uses, perhaps in combination with one or more of the volatile sesquiterpenoids in the Osage orange. However, since osajin is not a volatile component, repellency is less effective, i.e., only via contact.

Conclusion. Testing to date shows that steam distillates of various ripe Osage orange components performed better than components extracted by other means. This includes, but is not limited to, alpha-cubebene, elemol, as well as the osajin. Further, components of the Osage orange not yet tested, particularly the volatile sesquiterpenoids, may also be effective repellents. It may also be that a combination or blend of the various constituents of the Osage orange, together with a suitable carrier, will provide even better repellency than any of the individual components can achieve alone. Future testing using various concentrations of DEET and other concentrations of napthelene as comparisons, is also expected to be performed.

Example 3

The purpose of this test was to determine the means by which repellents, such as the various compounds tested in Example 1, are detected by an insect.

Insects. Cockroaches from the same source as in Examples 1 and 2 were used.

Standard and Comparison Compounds. DEET was purchased from Aldrich Chemicals.

Starting Materials. The steam distillate and purified isomers of catnip (nepetalactone) as described in Example 1 were used.

Testing Procedure. Male cockroaches were antennectomized by using a razor blade to remove the antennae as close to the head as possible. The cockroaches were allowed to recover from the procedure for 24 hours before being exposed to the test compounds in the bioassay described in Example 1.

Results. Comparisons between test compounds for the treated side were made using a paired t-test as shown in Table 9.

TABLE 9

Results of behavioral assay of antennectomized male cockroaches, and paired t-test comparison with non-antennectomized male cockroaches tested at the same concentration

| Treatment (μg/cm$^2$) | Mean seconds on treated side ± SEM | Calculated t-value | Mean seconds on untreated side |
|---|---|---|---|
| 1600 DEET | | | |
| Annectomized | 148 ± 17.1 | | 154 ± 17.2 |
| Non-antennectomized | 63.4 ± 15.9 | 3.03* | |
| 160 Z,E-Nepetalactone | | | |
| Annectomized | 121 ± 10.6 | | 180 ± 10.5 |
| Non-antennectomized | 65.4 ± 11.8 | 3.40* | |
| 80 E,Z-Nepetalactone | | | |
| Annectomized | 153 ± 15.2 | | 149 ± 15.3 |
| Non-antennectomized | 31.7 ± 5.2 | 7.84* | |

*Difference is significant by two-tailed paired t-test at α = 0.05, df = 9.

The cockroaches without antennae were indifferent to the repellents tested, as they spent nearly equal amounts of time on both sides of the filter paper.

Conclusion. The results of this testing demonstrates that chemoreceptors responsible for the repellent action of the compounds are located on the antennae of the German cockroach. It is likely that such chemoreceptors are located on the antennae of other arthropods having antennae as well.

Example 4

The purpose of this test was to determine if male cockroaches would be more sensitive than female cockroaches to test compounds in the same manner as DEET.

Testing methods and materials. In this experiment, female German cockroaches were tested in the same manner described in Example 1 against the steam distillates of catnip and the Osage orange. Testing using the commercial repellent, DEET, was also performed for comparison. It is known that male cockroaches are generally more sensitive to repellents, such as DEET, than female cockroaches.

Results. Table 10 shows the commercial standard, DEET, as compared with acetone against the female German cockroach. "L" and "R" refer to left and right sides of the filter paper.

TABLE 10

Female German cockroach testing - 10%* (1600 μg/cm$^2$) DEET vs. acetone

| trial | treated | untreated | treated on |
|---|---|---|---|
| 1 | 157 | 150 | L |
| 2 | 146 | 155 | L |
| 3 | 137 | 162 | R |
| 4 | 150 | 152 | L |
| 5 | 99 | 203 | R |
| 6 | 166 | 135 | L |
| 7 | 144 | 154 | L |
| 8 | 144 | 156 | R |
| 9 | 116 | 182 | R |
| 10 | 181 | 120 | L |
| mean | 144 | 156.9 | |
| SEM | 7.4 | 7.2 | |

*by volume

As can be seen, at the ten (10) % rate, DEET exhibits reduced repellency against female cockroaches as compared with the male cockroaches tested above since there was no significant difference between the treated and untreated sides. In comparison, the same ten (10) % DEET treatment resulted in 63 seconds on the treated side and 238 seconds on the untreated side as described in Example 1 (See Table 2).

Table 11 is a comparison of the essential oil of catnip, as compared with hexane against the female German cockroach.

TABLE 11

Female German cockroach testing - Five (5)%* (800 μg/cm$^2$) catnip steam distillate vs. hexane

| trial | treated | untreated | treated on |
|---|---|---|---|
| 1 | 107 | 197 | L |
| 2 | 80 | 221 | L |
| 3 | 90 | 212 | R |
| 4 | 67 | 235 | R |
| 5 | 86 | 217 | L |
| 6 | 210 | 91 | R |
| 7 | 127 | 174 | L |
| 8 | 163 | 139 | R |
| 9 | 120 | 182 | R |
| 10 | 89 | 212 | R |
| mean | 113.9 | 188 | |
| SEM | 13.8 | 13.9 | |

*by volume

The results shown in Table 11 demonstrate a very high repellency of the essential oil of catnip, i.e., nepetalactone, against the female German cockroach in many of the trials. Unlike DEET, however, which showed no significant repellency against female German cockroaches, the essential oil of catnip demonstrated very good repellency at the lower rate of about five (5) %.

Table 12 is a comparison of the essential oil of the ripe Osage orange with hexane against the female German cockroach.

TABLE 12

Female German cockroach testing - Two (2) ml ripe Osage orange steam distillate vs. hexane

| trial | treated | untreated | treated on |
|---|---|---|---|
| 1 | 109 | 193 | R |
| 2 | 118 | 186 | R |
| 3 | 138 | 166 | R |
| 4 | 138 | 166 | L |
| 5 | 153 | 148 | L |
| 6 | 151 | 153 | L |
| 7 | 150 | 151 | L |
| 8 | 122 | 184 | R |
| 9 | 131 | 172 | L |
| 10 | 63 | 239 | R |
| mean | 127.3 | 175.8 | |
| SEM | 8.5 | 8.5 | |

Again, in many of the trials, the essential oil of the Osage orange performed surprisingly well, exhibiting very good repellency against the female cockroach.

Conclusions. Several of the compounds and extracts tested performed better than the commercial standard, DEET, with regard to repellency against female cockroahes. These tests show that female cockroaches can be repelled by the essential oils of catnip and the Osage orange (although not to the same extent as the males). This is in accord with Scheffler and Dombrowski, 1992, *Insecticeds: Mechanism of Reaction and Resistance*, Andover, U.K. These results indicate that composition containing nepetalactone or, likely, one of its isomers, as well many of the components of the Osage orange, such as elemol, will likely be effective for use as an arthropod repellent, such as against the German cockroach.

Example 5

The purpose of this test was to determine a non-lethal dose of nepetalactone to two mosquito species, for use in the activity chamber described in Example 7.

Insects. Mixed sexes of wild *Aedes aegypti* collected initially in Costa Rica in 1999 were used in this testing. Mixed sexes of *Culex tarsalis* mosquitoes obtained from the University of California at Berkeley, in Berkeley, Calif., were also tested. Both types of mosquitoes are now maintained in the Entomology Department at Iowa State University, Ames, Iowa according to the following methods of rearing:

*Aedes aegypti*. Eggs from the mosquitoes are dried and stored in plastic bags in a refrigerator for several months. The date of storage is noted on the container. A section of paper towel containing the oldest eggs are then placed in deoxygenated water. Larvae typically emerge in minutes. Once the larvae have emerged, they are placed into a pan having about 2.5 to 3.7 cm (about one (1) to 1.5 in) of water. Two (2) to three (3) drops of Tetramin™ mix is added and the pans are labeled with the appropriate date. Tetramin™ is made by TetraWerke in Melle, Germany, and distributed in the United States by the Tetra Co. in Blacksburg, Va. One drop of Tetramin™ mix is added everyday until the larvae reach the third instar. The larvae are fed about one (1) to three (3) drops of Tetramin™ mix daily, depending on their progression of growth. If growth is poor, more drops are given. Fifty pupae are then collected in cups that are half-filled with distilled water. The cup is properly labeled and sealed with a mesh square and lid. A sucrose-saturated cotton ball is then placed on the mesh and flattened. After emergence of all mosquitoes in the cup, the mosquitoes are released into a labeled cage. A sedated live rabbit is placed on top of the cage about six (6) to seven (7) days after release for the mosquitoes to feed on for 15 to 20 minutes. Three days after feeding, a cup that is about half-full with distilled water and lined with a paper towel (i.e., oviposition dish) is placed in the cage. After two days, the cup is removed and the paper is dried to start the cycle again.

*Culex tarsalis*. Five (5) egg rafts are placed in a pan having about 2.5 to 3.7 cm (about one (1) to 1.5 in) of water. About two (2) to three (3) drops of Tetramin™ mix is added daily. Pans are checked daily for hatching. Typically, the first instars appear in about two (2) to three (3) days. One (1) drop of Tetramin™ mix is added every day until the larvae reach the third instar. One (1) to three (3) drops of mix is fed to the larvae daily, depending on progression of growth. Fifty pupae are collected in cups in cups that are half-filled with distilled water. The cup is properly labeled with date, species, number of pupae, etc. The cup is then sealed with a mesh square and lid. (Green tape is used to indicate anautogenous, with red tape used for autogenous). A sucrose-saturated cotton ball is then placed on the mesh and flattened. After emergence of all mosquitoes in the cup, the mosquitoes are released into a labeled cage. A sedated quail is placed on top of the cage about six (6) to seven (7) days after release for the mosquitoes to feed on for about 15-20 minutes. The sucrose pads are removed the day before feeding. Three days after feeding, the oviposition dish (described above) is placed in the cage. The dish is removed after two days, and egg rafts are separated to five (5) per pan to start the cycle again. If necessary, mosquitoes can be fed on quail again three (3) to four (4) days after oviposition.

Standards and Starting Materials. The essential oil of catnip isolated as described above was used in this test. Hexane, purchased from Fischer Scientific, Inc., was used as a control.

Test Procedure. Toxicity tests were conducted in the upper sections of a number of glass bottles. Specifically, each glass bottle was cut into two sections, and the bottom portion was discarded. The remaining upper portion had a volume of approximately 175-ml. The top of the upper portion had a ground glass mouth. The open bottom end was covered with a seven (7)-cm piece of filter paper, which was secured with all-purpose glue. The glue was allowed to dry and excess filter paper was trimmed by using a razor blade. One-half ml of hexane solution was applied to the filter paper. The hexane was allowed to dry for approximately one (1) minute. Parafilm® brand paraffin stretch wrap film made by American National Can Co. on Chicago, Ill., was placed on the outside of the bottle to seal the bottom of the bottle over the filter paper. Approximately five (5) adult mosquitoes (mixed sexes) were placed in the bottle through the mouth. The mouth was then plugged with a cotton ball that had been soaked in a ten (10) % sucrose solution. Mortalities were recorded at 0.5, 24, 48 and 120 hours.

Results. The results of this testing are shown in Table 13.

TABLE 13

Mosquito mortality at varying concentrations of nepetalactone derived from catnip

| Catnip essential oil concentration ($\mu g/cm^2$) | % Mortality | | | |
| --- | --- | --- | --- | --- |
| | 0.5 hr | 24 hr | 48 hr | 120 hr |
| *Aedes aegypti* | | | | |
| 130 | 26 | 100 | 100 | 100 |
| 65 | 37 | 100 | 100 | 100 |
| 13 | 3 | 100 | 100 | 100 |
| 6.5 | 3 | 24 | 27 | 27 |
| 1.3 | 0 | 3 | 3 | 3 |
| Hexane control | 4 | 7 | 7 | 7 |
| Blank control | 0 | 10 | 10 | 10 |
| *Culex tarsalis* | | | | |
| 65 | 0 | 100 | 100 | 100 |
| 13 | 0 | 100 | 100 | 100 |
| 6.5 | 0 | 50 | 61 | 93 |
| 1.3 | 0 | 19 | 31 | 69 |
| Hexane control | 0 | 20 | 20 | 36 |

The above results demonstrate that the individual isomers of catnip as well as the essential oil of catnip, are each toxic to adult mosquitoes in a closed system. Such results could be due to fumigation or to contact toxicity.

Conclusion. Studies undertaken to determine sub-lethal concentrations of nepetalactone yielded surprisingly high toxicity in contact/fumigation bioassays.

Example 6

The purpose of this test was to study the repellency of mosquitoes, flies and cockroaches in a static air environment, at concentrations that are nonlethal.

Insects

*Blattella germanica*. The German Cockroach was obtained from the same source as in Example 1.

*Musca domestica* (house flies). The flies were of mixed sexes (Cornell strain) and were reared from eggs collected from an existing colony at the Pesticide Toxicology Laboratory, Iowa State University, Ames, Iowa. Adult flies were allowed a 24-hr oviposition period for egg deposition onto a moistened rearing media. The rearing media provided was a mixture of Fly Diet (LabDiet, St. Louis, Mo.), yeast, sugar and distilled water. After the egg-laying period, eggs were transferred to a 12"×5" pan filled with rearing media and contained inside a larger pan, 20"×7", with sand (larval pan). This larval pan was kept in an incubator at 75° F. for 1 week during larval growth and maturation. At the end of 1 week, larvae moved out of the rearing media pan and pupated in the surrounding sand. The rearing media was then removed from the larval pan and water was added to float the pupae and ease in collection. Approximately 250 pupae were placed in a single 12"×12"×12" screened cage with distilled water and a mixture of sugar and powdered milk (1:1) for food. See, for example, Clegern, Robert W., *Population Dynamics and Environmental Stress Studies of House Flies in the Laboratory*. PhD Thesis-University of Illinois at Urbana-Champaign. 1972. DNALDISS-73-9, 907, Ann Arbor, Mich.

*Culex pipiens* (Northern House Mosquito). The mosquitoes tested here were obtained from a colony ten generations removed from wild mosquitoes collected in Ames, Iowa, was used for testing. The colony was blood-fed on the bobwhite quail, *Colinus virginianus*. Eggs from mosquitoes were dried and stored in an incubator until needed. Eggs were placed in deoxygenated water and two to three drops of a ground TetraMin™ fish food solution were added to the water to feed the larvae. Pupae were removed from the larval pans as they appeared and were placed into mesh-covered paper cups. Following emergence, adult females were tested over a six-day period. The mosquitoes were continually allowed to feed on a cotton ball soaked with 0.3 M sucrose solution. At 1-2 hours before testing began, the cotton balls were removed, and the mosquitoes were preconditioned in the bioassay environmental chamber, held at 26° C., for 1-2 hours.

Repellency Bioassay Methods

German Cockroach and House Fly Bioassay.

A choice-test arena was used to assess irritancy of test solutions to two common household insect pests, the German cockroach (*Blattella germanica*) and the house fly (*Musca domestica*). Catnip essential oil obtained by steam distillation of catnip obtained from the same source as described in the above examples, and the two major components of its essential oil, Z,E-nepetalactone and E,Z-nepetalactone (isolated from the essential oil by preparative TLC), were evaluated for behavioral effects of contact irritancy to the German cockroach. The TLC was performed as described in McElvain, S. M. et al., *J. Am. Chem. Soc.*, 1941, 63, 1558-1563. Catnip essential oil and its major constituent Z,E-nepetalactone were tested against the house fly. N,N-diethyl-m-toluamide (DEET) (Aldrich, St. Louis, Mo.) served as a positive control for the choice-test arena assay and as a point of comparison for measuring insect behavioral effects that result from current commercial insect repellents. Test solutions ranging from 10% to 0.1% (vol/vol) active ingredient (a.i.) were made up in acetone and then delivered on to a filter paper for solvent evaporation. Resulting rates of the active ingredient were 1.63 mg/cm$^2$, 815 $\mu g/cm^2$, 163 $\mu g/cm^2$, 81.5 $\mu g/cm^2$, and 16.3 $\mu g/cm^2$. Choice-test are for German cockroaches and house flies were constructed from plastic Petri dishes. One-half of a 12.5-cm dia. filter paper was treated with 1 ml test solution, and the other was treated with 1 ml of only solvent (control). Both halves of the filter paper were placed in the choice-test arena. Position of the treated filter paper was randomized using a random-number table.

Individual German cockroaches or house flies were placed in each choice-test arena through a centered hole in the lid of the Petri dish and evaluated for a 300-second period. The amount of time the insect spent on the treated and untreated filter papers were recorded and used to calculate a percentage repellency value:

Percentage Repellency=((Time on Untreated−Time on Treated)/300)×100

Ten replicates of each treatment solution were tested for both German cockroaches and house flies. Details of this assay design and some results have previously been described.

Mosquito Repellency.

A colony of *Culex pipiens*, obtained from the same source as described above was used.

Percentage and Contact Repellency Bioassay

A static-air choice-test apparatus as described above was used to determine the behavioral effects on the insects in this study. The apparatus consisted of a 9×60-cm section of glass tubing with a 2-cm hole drilled at the midpoint along the length for central introduction of the insects. All of the testing was conducted in an environmental chamber at 26° C.

Treatments included catnip essential oil, obtained by steam distillation as described herein and in Peterson, et al., *J. Econ. Entomol.*, 2002, 95, 377-380. Osage orange essential oil, obtained by steam distillation of whole fruits previously described in Peterson, et al., *J. Essential Oil Res.*, 2002, 14, 233-236, elemol (Augustus Oils, New Hampshire, England), and DEET (Aldrich, St. Louis, Mo.) test solutions at 1%, 0.5% and 0.1% concentrations (wt/vol). The test solutions' solvent, hexane, served as a control treatment in this assay.

One milliliter of the solution was applied to one half of a 9-cm diameter round filter paper with an area of 63.6 cm$^2$ and then allowed to dry before testing. This resulted in the following rates of exposure: 157, 78.6 and 15.7 µg/cm. Treated filter papers were placed inside the lids of 9-cm glass petri dishes, and placed over the ends of the glass tube. The position of the treated side, to the right or to the left, was selected by using a random-number table. Approximately fifteen unmated adult female mosquitoes were anaesthetized with $CO_2$ and then introduced to the 9×60-cm glass cylinder through the centered 2-cm hole. Timing began two minutes after mosquito introduction, and mosquito distribution inside the static-air choice-test apparatus was observed over a 180-minute period for each treatment. Mosquito distribution (number of individuals on treated and untreated side) was recorded at 15, 30, 60, 90, 120, and 180-minute timepoints.

The data generated by this study was used to examine two measures of mosquito repellency, percentage repellency and contact repellency. Percentage repellency was calculated for with the following formula: Percentage Repellency=((Number of Individuals on Untreated Half−Number of Individuals on Treated Half)/15)×100.

Contact repellency was defined in this assay as 100% avoidance of the treated filter paper (no contact). 15, 30, 60, 90, 120, and 180-minute time-points were used to assess contact repellency for individual observations.

The experimental design was a completely randomized design using three replications of each treatment. Analysis of variance was performed on SAS (PROC GLM; SAS Version 8) to identify significant differences of percentage repellency due to treatment, and concentration. Multiple comparisions were completed using Tukey's procedure. Treatment pairwise comparisons of contact repellency, which included data from the six time-points observed for each treatment, were completed using Fishers Exact (PROC FREQ; SAS Version 8).

Mosquito Residual Repellency Bioassay

Aged applications of catnip essential oil, elemol, DEET, and hexane (control) were compared in the static-air choice-test apparatus under the same conditions as described above. The 0.5% and 0.1% (wt/vol) solutions of each test solution were made to yield the same rate of active ingredient used in the above mosquito repellency bioassay. Individually treated filter papers were then placed in a fume hood and aged for 0, 30, 60, 120, or 180-minutes, allowing volatization to occur over a set period of time. After the specified ageing period, filter papers were placed on the inside of the 9-cm glass petri dish lids, and then placed over the ends of the glass tube. The position of the treated side was randomized. Approximately 18 unmated adult female mosquitoes were anaesthetized with $CO_2$ and then introduced to the 9×60-cm glass cylinder through the centered 2-cm hole. Timing began 2 minutes after mosquito introduction, and mosquito distribution (number of individuals on treated and untreated sides) inside the static-air choice-test apparatus was recorded after 15 minutes for determination of Percentage Repellency (calculations shown under Percentage and Contact Repellency Bioassay). Experimental design was completely randomized with three replications of each aged test solution. Analysis of variance was used to identify significant differences related to active ingredient, concentration, and ageing period. Regression analysis was used to examine percentage repellency relationship to filter paper ageing.

Results

German Cockroach and House Fly Repellency

The German cockroach and house fly both showed contact irritancy responses to at least one concentration of each test solution evaluated (Table 14). German cockroaches gave the highest percentage repellency value response when exposed to the 0.5% solution of E,Z-nepetalactone. This percentage repellency response was more than four times the response seen from testing the same concentration of Z,E-nepetalactone. In the cockroach experiment, both Z,E- and E,Z-nepetalactone isomers caused an overall higher percentage repellency response at lower concentrations of the respective active ingredient, compared to treatments with DEET. The house fly responded to the test solutions with a similar trend, although the E,Z isomer was not tested. The higher percentage repellency values resulted from exposure to catnip essential oil and to Z,E-nepetalactone, ranging from 70-96%, compared to DEET (39%) (Table 15).

TABLE 14

Percentage repellency of catnip essential oil, Z,E-nepetalactone, E,Z-nepetalactone, DEET and control to the German cockroach, *Blattella germanica*, in the choice-test arena bioassay.

| Treatment | Application Rate | Percentage Repellency ± SEM |
| --- | --- | --- |
| Controls | Acetone | 5.2 ± 7.5a |
|  | Hexane | 2.9 ± 3.7a |
| DEET | 1.60 mg/cm$^2$ | 58.3 ± 10.5b |
|  | 800 µg/cm$^2$ | 25.8 ± 9.5a |
|  | 160 µg/cm$^2$ | 20.4 ± 9.2a |
|  | 80 µg/cm$^2$ | 15.5 ± 5.4a |
| Catnip Essential Oil | 800 µg/cm$^2$ | 55.6 ± 9.8b |
|  | 160 µg/cm$^2$ | 27.7 ± 13.1ab |
|  | 80 µg/cm$^2$ | 33.7 ± 15.7ab |
| Z,E-Nepetalactone | 800 µg/cm$^2$ | 68.2 ± 5.7b |
|  | 160 µg/cm$^2$ | 56.8 ± 7.8b |
|  | 80 µg/cm$^2$ | 15.4 ± 6.9a |
|  | 16 µg/cm$^2$ | 16.1 ± 7.4a |
| E,Z-Nepetalactone | 80 µg/cm$^2$ | 79.4 ± 3.5c |
|  | 16 µg/cm$^2$ | 46.4 ± 11.0b |

Treatments with the same letter are not significantly different by least-squares means analysis at $\alpha = 0.05$ (See Peterson, J. Econ. Entomol, 2002, 95, 377-380).

TABLE 15

Percentage repellency of DEET, catnip essential oil, Z,E-nepetalactone, and control to the house fly, *Musca domestica*, in the choice-test arena bioassay.

| Treatment | Application Rate | Percentage Repellency |
|---|---|---|
| Control | — | −5.3 |
| DEET | 800 µg/cm$^2$ | 20.7 |
| | 160 µg/cm$^2$ | 19.3 |
| | 80 µg/cm$^2$ | 38.7 |
| Catnip Essential Oil | 80 µg/cm$^2$ | 63.3 |
| | 160 µg/cm$^2$ | 70.0 |
| | 80 µg/cm$^2$ | 52.7 |
| Z,E-Nepetalactone | 800 µg/cm$^2$ | 96.0 |
| | 160 µg/cm$^2$ | 69.3 |
| | 80 µg/cm$^2$ | 87.3 |

See Peterson, et al., J. Essent. Oil Res., 2002, 14, 233-236.

Mosquito Repellency

Figure 8:
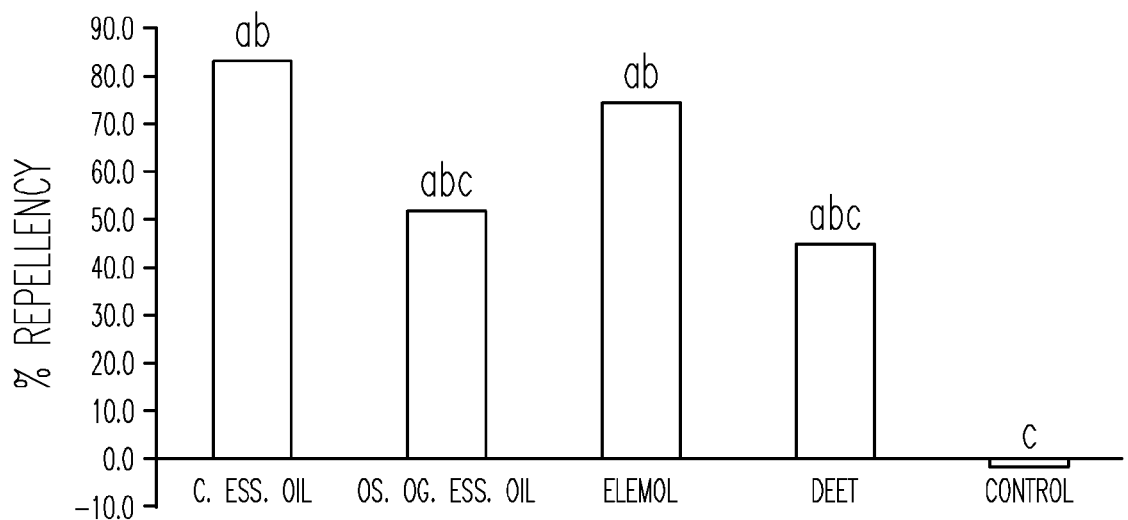
FIG. 8 shows percentage repellency (15 minutes) of the northern house mosquito, Culex pipiens, in a static-air repellency chamber to a 157 µg/cm$^2$ application (1% concentration) of catnip essential oil, elemol, DEET, Osage orange essential oil and a solvent control, in embodiments of the present invention.
Figure 9:
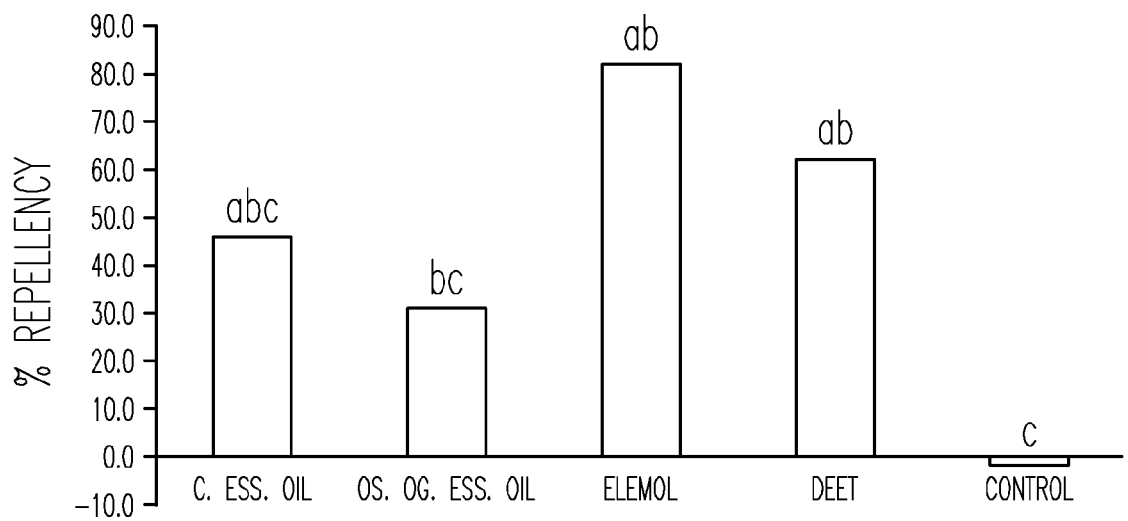
FIG. 9 shows percentage repellency (15 minutes) of the northern house mosquito, Culex pipiens, in a static-air repellency chamber to 78.6 µg/cm$^2$ application (0.5% concentration) of catnip essential oil, elemol, DEET, Osage orange essential oil and a solvent control, in embodiments of the present invention.
Figure 10:
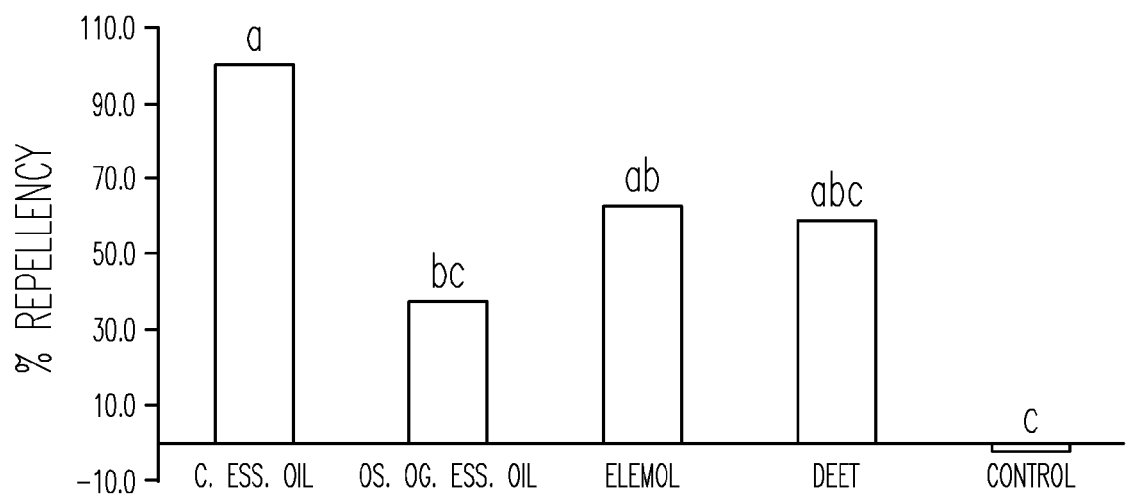
FIG. 10 shows percentage repellency (15 minutes) of the northern house mosquito, Culex pipiens, in a static-air repellency chamber to 15.7 µg/cm$^2$ application (0.1% concentration) of catnip essential oil, elemol, DEET, Osage orange essential oil and a solvent control, in embodiments of the present invention.

Percentage repellency of catnip and Osage orange essential oil, elemol and DEET at 15 minutes is represented in FIGS. 8, 9 and 10. Treatments with the same letter are not significantly different by Tukey analysis at α=0.05. Additionally, test results showing between +15% and −15% repellency (i.e., attractancy) are typically not statistically different from zero such that no quantifiable effect can be claimed. See, for example, the results for the control in FIGS. 8-10 and 11-13. Such small variations from zero are interpreted herein as the result of experimental error or randomness in the behavior of the insects.

FIG. 8 shows percentage repellency (15 minutes) of the northern house mosquito, *Culex pipiens*, in a static-air repellency chamber to a 157 µg/cm$^2$ application (1% concentration) of catnip essential oil, elemol, DEET, Osage orange essential oil and a solvent control.

FIG. 9 is a 15-minute percentage repellency of the northern house mosquito, *Culex pipiens*, in a static-air repellency chamber to 78.6 µg/cm$^2$ application (0.5% concentration) of catnip essential oil, elemol, DEET, as well as Osage orange essential oil, and a solvent control. this was already said above wrt all of the figures.

FIG. 10 is a 15-minute percentage repellency of the northern house mosquito, *Culex pipiens*, in a static-air repellency chamber to 15.7 µg/cm$^2$ application (0.1% concentration) of catnip essential oil, elemol, DEET, as well as Osage orange essential oil, and a solvent control.

All compounds tested showed various levels of significance in percentage repellency and contact repellency. The overall concentration effect was not significant (P=0.4569). Osage orange essential oil represented the lowest values in percentage repellency (<60%) and did not show any significant contact repellency (P=0.1). Catnip essential oil showed high percentage repellency at the 15-minute time-point at all concentrations tested, including the highest value, 100% from the 0.1% concentration (FIG. 8). This was also the most significant level of contact repellency (P<0.0001) resulting from the three concentrations of catnip essential oil (Table 16). The other concentrations of catnip essential oil varied in contact repellency (0.5%) concentration, P=0.5, and 1% concentration, P=0.02.

Elemol solutions yielded the second highest set of percentage repellency values of the test solutions, ranging from 81% to 63%. These treatments also resulted in highly significant contact repellency (Table 16). The commercially available standard for mosquito repellency, DEET, also showed high percentage repellency values, ranging from 63% to 44%, in addition to high significance for contact repellency.

TABLE 16

Contact repellency of the northern house mosquito, *Culex pipiens*, measured at 15, 30, 60, 90, 120, 180-minutes in a static-air repellency chamber to catnip essential oil, Osage orange essential oil, elemol, DEET, and control. P-values in the table are from Fisher Exact test.

| Treatment | Application Rate | Treatment vs. Control P value |
|---|---|---|
| Catnip Essential Oil | 157 µg/cm$^2$ | 0.02 |
| | 78.6 µg/cm$^2$ | 0.5 |
| | 15.7 µg/cm$^2$ | <0.001 |
| Osage Orange Essential Oil | 157 µg/cm$^2$ | 0.1 |
| | 78.6 µg/cm$^2$ | 0.5 |
| | 15.7 µg/cm$^2$ | 0.5 |
| Elemol | 157 µg/cm$^2$ | <0.001 |
| | 78.6 µg/cm$^2$ | <0.001 |
| | 15.7 µg/cm$^2$ | <0.001 |
| DEET | 157 µg/cm$^2$ | <0.001 |
| | 78.6 µg/cm$^2$ | <0.001 |
| | 15.7 µg/cm$^2$ | <0.001 |
| Control | — | — |

As a comparison, Table 17 shows data on spatial repellency of 1%, 0.5%, and 0.1% concentrations (equivalent to 157 µg/cm$^2$, 78.6 µg/cm$^2$, and 15.7 µg/cm$^2$, respectively). The catnip essential oil is most potent spatially (at 15 minutes, the usual time period tested). Elemol is next most potent, followed by DEET and then Osage orange essential oil. All are repellent in a statistically significant level, although the Osage orange was only repellent at the 1% concentration. The potential for Osage orange essential oil is still good, since all commercial repellents are now sold in formulations (sprays, lotions, creams, solutions) with 5% to 50% or higher active ingredient.

TABLE 17

Percentage repellency of *Culex pipiens* to catnip essential oil, Osage orange essential oil, elemol, DEET and untreated surface (control).

| | Concentration (%) | Percentage Repellency | Std. Dev | Tukey Grouping | Sig. Diff. w/ Control |
|---|---|---|---|---|---|
| Catnip Essential Oil | 1 | 83.2 | 9 | ab | * |
| | 0.5 | 45.4 | 22 | abc | * |
| | 0.1 | 100.0 | 0 | a | * |
| Osage Orange Essential Oil | 1 | 51.9 | 6 | abc | * |
| | 0.5 | 30.4 | 24 | bc | |
| | 0.1 | 37.4 | 29 | bc | |
| Elemol | 1 | 74.1 | 23 | ab | * |
| | 0.5 | 81.3 | 23 | ab | * |
| | 0.1 | 63.0 | 6 | ab | * |
| DEET | 1 | 44.4 | 19 | abc | |
| | 0.5 | 62.3 | 28 | ab | * |
| | 0.1 | 59.3 | 36 | abc | * |
| Control | — | −1.7 | 9 | c | — |

A multiple comparison test used to determine which means in a set differ from the rest. Means followed by the same letter are not significantly different.

Residual Repellency

Percentage repellency values were high for catnip essential oil, elemol, and DEET solutions immediately following application to the test surface (Table 18). The analysis of variance showed that there was a difference among the three different solutions and the control (P<0.0001), and a significant interaction with treatment solution and time (P=0.0019). The only treatment solutions to show a significant decrease in percentage repellency over time were 0.5% catnip essential oil (P=0.02) and 0.1% catnip essential oil (P=0.003) in which 51% of the variability in the data was explained by this negative linear relationship. Elemol, DEET, and control treatments did not show significant trends in the regression analysis, indicating maintenance of repellency with elemol and DEET over the 3-hour period.

TABLE 18

Residual percentage repellency of the northern house mosquito, *Culex pipiens*, to 0, 30, 60, 90, 120, 180-minute aged treatments of 0.5% and 0.1% solutions of catnip essential oil, elemol, DEET, and control in a static-air repellency chamber.

| Treatment | Application Rate | Percentage Repellency Over Time | | | | |
|---|---|---|---|---|---|---|
| | | 0 min | 30 min | 60 min | 120 min | 180 min |
| Catnip Essential Oil | 78.6 µg/cm$^2$ | 71.5 | 88.6 | 59.8 | 24 | 31.9 |
| | 15.7 µg/cm$^2$ | 88.8 | 37 | 40.7 | 22.2 | 7.4 |
| Elemol | 78.6 µg/cm$^2$ | 84.7 | 76.5 | 96.5 | 80.8 | 76.5 |
| | 15.7 µg/cm$^2$ | 35.0 | 30.8 | 49 | 20.7 | 44.8 |
| DEET | 78.6 µg/cm$^2$ | 74.0 | 37 | 59 | 77.7 | 74 |
| | 15.7 µg/cm$^2$ | 54.9 | 23.1 | 45.7 | 39 | 70.6 |
| Control | — | −6.1 | −9.3 | 1.3 | 25.5 | −9.1 |

Conclusions

Bioassays in a choice-test arena were used to assess cockroach and house fly irritancy responses. The use of deterrents is a valuable tool for pest control, particularly when used with an integrated pest management program. In the studies we report, contact irritancy serves as a measure of deterrence and helps to identify compounds that may serve as effective protectants for premises. It should be noted that limitations of this method are that individuals are only exposed to the treated surface for a 5-minute period and can only characterize a short-term response.

German cockroaches and house flies responded negatively to all solutions evaluated. These results demonstrate the efficiency of the assay and add support for catnip essential oil as an insect repellent. Specifically, cockroaches showed greatest avoidance of filter papers treated with the purified nepetalactone isomers, Z,E and E,Z, and house flies showed greatest avoidance of Z,E-nepetalactone. Both nepetalactone isomers were compared during trials on the German cockroach, and the result was a much higher percentage repellency from papers treated with E,Z-nepetalactone. These results raise the need for structure-activity relationship studies, since Z,E-nepetalactone and E,Z-nepetalactone are very similar compounds that only differ in orientation of groups across one bond on the molecule. Additional studies on the mode of action of deterrents are required before conclusions are drawn on how the minimal structural difference in Z,E and E,Z-nepetalactone cause significantly different responses from *B. germanica*.

Initial investigations of mosquito repellency with catnip and Osage orange essential oil allowed us to directly compare with DEET, the current commercial standard, and further analysis helped identify differences in the activity of these compounds as insect repellents. At present, there is no one characteristic that fits all repellents or a single mechanism that explains how specific chemicals and blends act on insects. Studies have shown that an insect's response to the chemicals in the environment is dependent on their physiological and developmental state (14). The studies presented in this report focus on adult female mosquitoes and their responsiveness to various rates of catnip and Osage orange essential oil, elemol and DEET over time. Results from mosquito repellency assay show that after 15-minutes, the northern house mosquito was most significantly repelled from the filter paper surfaces treated with catnip essential oil (100%). The percentage repellency values from the DEET and elemol treatments resulted in a lower range (81%-44%) than catnip essential oil, but showed higher contact repellency. Observations during the assay showed that individuals exposed to catnip essential oil moved further away from the treated surface than in the DEET and elemol treatments. Over time, this effect started to decrease with catnip essential oil as mosquitoes redistributed through the tube, eventually reaching a distribution similar to the control.

Mosquitoes exposed to DEET and elemol settled far enough from the treated surface to achieve an adequate level of contact repellency. As time increased, individuals would continually reject the treated surface up to the end of the 180-minute period, unlike the catnip essential oil, which exhibited an initially high repellency response that decreased over time. DEET and elemol showed a longer duration of repellency compared to catnip essential oil, as is evidenced with higher significance in contact repellency. Additional studies are needed to better understand how these differences occur, including studies on the chemical volatilization, and interference with behavioral stages of mosquito host-finding and acceptance.

The second mosquito assay focused on quantifying the residual repellency of the northern house mosquito to aged filter papers of catnip essential oil, elemol and DEET. All 0.5% and 0.1% test solutions showed significant percentage repellency following application (i.e., with no ageing period). This repellency effect slowly decreased over time for both concentrations of catnip essential oil (0.5%, P=0.02, 0.1%, P=0.003). There was no significant loss in percentage repellency seen in the DEET and elemol treatment solutions, accounting for continual mosquito repellency over 3 hours from a treated surface. Olfactory repellency differs from contact repellency, and the method used here allows for some differentiation between the two types. The high initial spatial repellency of catnip essential oil is not sustained over a 3-hour period, but elemol and DEET do show residual repellency to that time-point.

Example 7

The purpose of this test was to determine the spatial and contact repellency of various biorational agents to the *Aedes aegypti* mosquito.

Insects

Yellow Fever Mosquito (*Aedes aegypti*). Mosquitoes obtained from University of Wisconsin in 2005 (which originated in Liverpool, England) were tested. They were kept in the same manner as described in Example 5.

Starting Materials

Catnip. Catnip was obtained from the source as described above in Example 1.

Elemol. Elemol was obtained from Augusta Chemical Limited having offices in the United Kingdom.

*Amyris* essential oil (*Amyris balsamifera*). For the testing in Example 7, *Amyris* essential oil was obtained from Phoenix Natural Products (NP), having offices in Middlesex, United Kingdom.

Control. Hexane having a purity in excess of 99% was purchased from Fischer Scientific Inc. having offices in Pittsburgh, Pa. Hexane was also used as the carrier together with the various compounds tested.

Test Equipment. In this testing, a static air repellency chamber was used. The apparatus consisted of a 9×60-cm section of glass tubing with a 2-cm hole drilled at the midpoint along the length for central introduction of the insects. All of the testing was conducted in an environmental chamber at ambient temperatures.

Test Methods. The data for spatial repellency was collected at 15 minutes after the introduction of female yellow fever mosquitoes into a static air repellency chamber. Data for the contact repellency was collected after three hours. The concentrations used in the tests are 1% solution (1 ml of it on a 9-cm diameter filter paper). One (1) ml of a 1% (wt/vol) solution of repellent substance containing hexane as a carrier was pipetted onto a 9-cm diameter filter paper results in a concentration of 157 μg/cm². The solution contained the desired mass of compound to be tested added to the desired volume of hexane, e.g., for a 1% solution of catnip essential oil, 1 mg was added to 100 ml of hexane.

One milliliter of the solution was applied to one half of a 9-cm diameter round filter paper with an area of 63.6 cm² and then allowed to dry before testing. Therefore the rate of exposure was 157 μg/cm². Treated filter papers were placed inside the lids of 9-cm glass petri dishes, and placed over the ends of the glass tube. The position of the treated side, to the right or to the left, was selected by using a random-number table. Approximately fifteen unmated adult female mosquitoes were anaesthetized with $CO_2$ and then introduced to the 9×60-cm glass cylinder through the centered 2-cm hole. Timing began 2 minutes after mosquito introduction, and mosquito distribution inside the static-air choice-test apparatus was observed over a 15-minute period for each treatment to determine spatial repellency. Basically the number of mosquitoes in the non-treated half were considered to be repelled and were counted. Percent repellency was considered to be: (Number of Individuals on Untreated Half−Number of Individuals on Treated Half)/15)×100. Contact repellency was defined in this assay as 100% avoidance of the treated filter paper-after three hours. The experimental design was a completely randomized design using six replications of each treatment.

Results. Table 19 shows 15-minute repellency and contact repellency of adult female yellow fever mosquitoes, *Aedes aegypti*, measured in six replications in a static-air repellency chamber to catnip essential oil, *Amyris* essential oil, catnip essential oil/*Amyris* essential oil mixture, and catnip essential oil/elemol mixture at 157 μg/cm² (1% solution).

Figure 11:
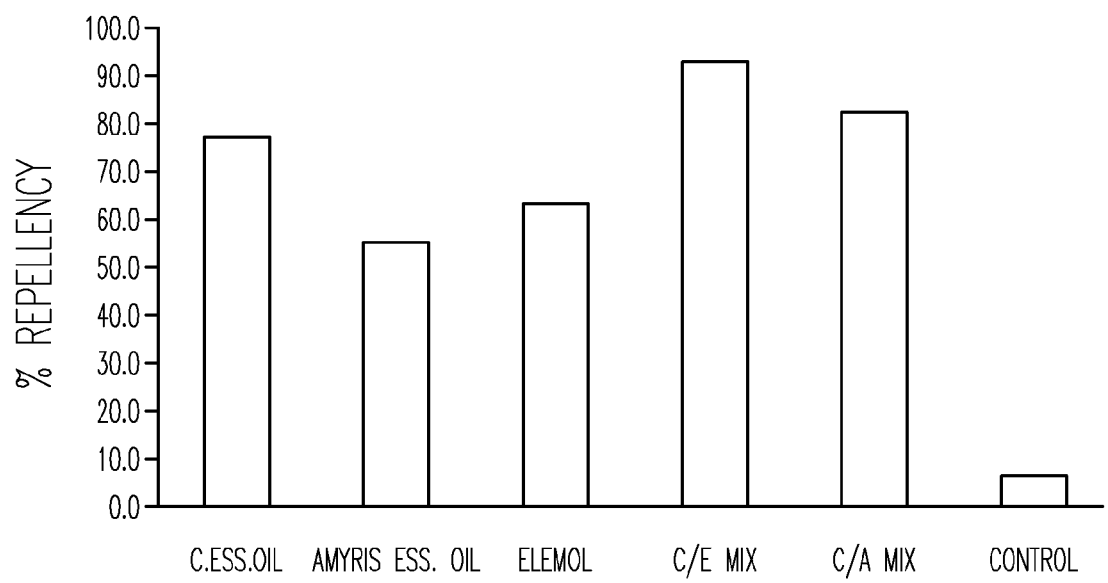
FIG. 11 shows percentage repellency (15 minutes) of adult female yellow fever mosquitoes, Aedes aegypti, measured in six replications in a static-air repellency chamber to catnip essential oil, Amyris essential oil, catnip essential oil/Amyris essential oil mixture, and catnip essential oil/elemol mixture at 157 µg/cm$^2$ (1% solution), in embodiments of the present invention.

FIG. 11 shows percentage repellency (15 minutes) of adult female yellow fever mosquitoes, *Aedes aegypti*, measured in six replications in a static-air repellency chamber to catnip essential oil, *Amyris* essential oil, catnip essential oil/*Amyris* essential oil mixture, and catnip essential oil/elemol mixture at 157 μg/cm² (1% solution).

As Table 19 shows, catnip is a very good spatial repellent at the 15-minute time period, but it is not significantly active as a contact repellent over the whole 3-hour time period (P value=0.2186). The *Amyris* essential oil is a moderately good spatial repellent (55.2%) at the 15-minute time period, and it showed extremely significant efficacy as a contact repellent over the 3-hour time period (P value is <0.0001). Elemol has a repellency profile similar to the *Amyris* essential oil. This is not surprising since *Amyris* essential oil contains major quantities of elemol and a close structural analog, eudesmol. Data are also shown for two mixtures of repellents: catnip essential oil/elemol and catnip essential oil/*Amyris* essential oil, both at a 1:1 ratio of the components. These mixtures exhibit strong spatial repellency (93% and 82.6%), even stronger than catnip essential oil alone (77%); the two mixtures also exhibit very strong contact repellency over the 3-hour time period, as indicated by the P values <0.0001 for their difference from the control treatment. The two mixtures provide an ideal profile of insect-repellent activity, i.e., excellent efficacy as a spatial repellent and excellent efficacy as a contact repellent, over the 3-hour time period. Other data from our lab indicates that elemol and *Amyris* essential oil are good spatial and very good contact repellents over a 6-hour time period. We are testing eudesmol, the catnip/elemol mixture, the catnip/*Amyris* essential oil mixture, and a catnip/eudesmol mixture over a 6-hour test period, with the expectation that all four will be very good contact repellents over the 6-hour period and that the three mixtures will be highly effective as both spatial and contact repellents.

Although mixtures tested were combined in a ratio of 1:1 it is likely that other proportions will also work.

Example 8

All test methods were the same as described in Example 7, except spatial repellency over a longer period.

TABLE 19

The 15-minute spatial repellency and 3-hour contact repellency of adult female yellow fever mosquitoes, *Aedes aegypti*, of various biorational repellents.

| Treatment | Conc (%) | Repellency (%)[a] | Std. Dev. | Significantly Different[b] | Avoidance Frequency[c] | Contact Rep.[d] w/ Control (P value) |
|---|---|---|---|---|---|---|
| Catnip Essential Oil | 1 | 77.7 | 14 | * | 19 | 0.2186 |
| Amyris Essential Oil (Phoenix NP) | 1 | 55.2 | 23 | * | 97 | <0.0001 |
| Catnip/Elemol Mixture (1:1) | 1 | 93.0 | 11 | * | 83 | <0.0001 |
| Catnip/Amyris Mixture (1:1) | 1 | 82.6 | 20 | * | 94 | <0.0001 |
| Elemol | 1 | 63.6 | 53 | * | 97 | <0.0001 |
| Control | — | 6.8 | 17 | — | 19 | — |

[a] % Repellency was determined at 15 minutes.
[b] Significantly differed from control (α = 0.05).
[c] Avoidance Frequency = average of mosquito contact repellency over 3-hour time period.
[d] Contact Repellency = 100% of the individuals off treated surface.

TABLE 20

Percentage Repellency over time of *Aedes aegypti* to elemol (practical grade), citronellal, DEET, Amyris essential oil (Phoenix Natural Products Ltd.), and an untreated surface (control) in a static-air olfactometer.

| Treatment | Application Rate | Average Percentage Repellency Over Time | | | |
|---|---|---|---|---|---|
| | | Initial | 60 min | 120 min | 360 min |
| Elemol | 78.6 mg/cm$^2$ | 56 | 52 | 43 | 35 |
| Citronellal | 78.6 mg/cm$^2$ | 79 | 10 | 19 | 1 |
| DEET | 78.6 mg/cm$^2$ | 52 | 64 | 47 | 49 |
| Amyris | 78.6 mg/cm$^2$ | 56 | 31 | 55 | 60 |
| Control | — | 16 | −12 | −14 | 0 |

These results demonstrate that *Amyris* essential oil, DEET and elemol all exhibit long term repellency.

Example 9

The purpose of this test was to determine the spatial and contact repellency of various biorational agents to the *Aedes aegypti* mosquito.

Starting Materials.

*Amyris* essential oil. *Amyris* essential oil from Phoenix (NP) and *Amyris* essential oil from Essential Oil University (EOU), a corporation having offices in Southall, Middlesex, United Kingdom, were tested. *Amyris* essential oil was purchased for testing because it was reported to have high amounts of elemol and eudesmol in it, which are the two predominant repellents in the Osange orange. However, individual isomers of both elemol and eudesmol are also present in *Amyris* essential oil. Both elemol and eudesmol occur in much higher percentages in *Amyris* essential oil than in Osage orange essential oil. Using conventional gas chromatography/mass spectrometry methods known in the art, we have confirmed high amounts, i.e., over 50% by weight of oil, of both sesquiterpenoids in the *Amyris* essential oil from Phoenix NP. However, it appears that the *Amyris* essential oil from EOU has a different composition.

Elemi. Elemi was obtained from Phoenix NP.

Control. Hexane having a purity in excess of 99% was purchased from Fischer Scientific Inc. Hexane was also used as the carrier together with the various compounds tested.

Test Methods. The test methods as described in Example 1 were used except the concentrations were 0.5% solution (1 ml of it on a 9-cm diameter filter paper) One (1) ml of a 0.5% solution of a repellent material pipetted onto that size filter paper results in 78.6 μg/cm$^2$. Also only three replications were used instead of six.

Results. Table 21 shows Percent Repellency and Contact repellency of *Aedes aegypti* to elemi essential oil, *Amyris* essential oil (Phoenix Natural Products Ltd.), *Amyris* essential oil (Essential Oil University), elemol (practical grade), and an untreated surface (control) in a static-air olfactometer.

Figure 12:
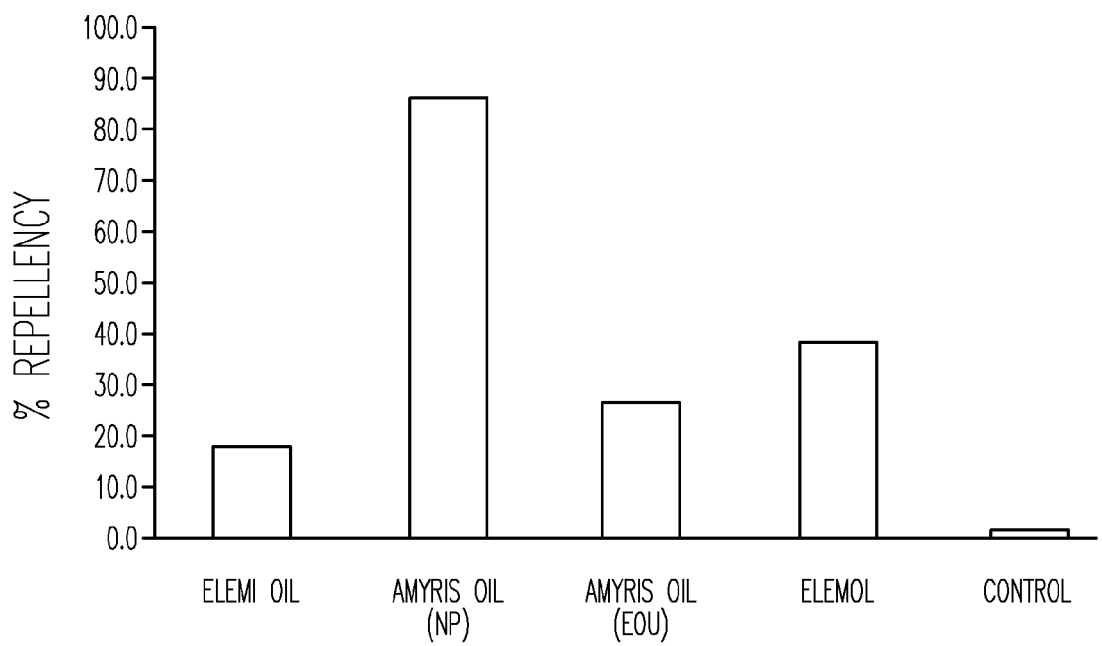
FIG. 12 shows percentage repellency (15 minutes) of adult female yellow fever mosquitoes, Aedes aegypti, measured in three replications in a static-air repellency chamber to elemi essential oil, Amyris essential oil (Phoenix Natural Products Ltd.), Amyris essential oil (Essential Oil University), elemol (practical grade), and an untreated surface (control), in embodiments of the present invention.

FIG. 12 shows percentage repellency (15 minutes) of adult female yellow fever mosquitoes, *Aedes aegypti*, measured in three replications in a static-air repellency chamber to elemi essential oil, *Amyris* essential oil (Phoenix Natural Products Ltd.), *Amyris* essential oil (Essential Oil University), elemol (practical grade), and an untreated surface (control).

Table 21 shows two oils are effective spatial repellents at half the concentration utilized in Table 1, i.e., 78.6 μg/cm$^2$ (obtained by treating the filter paper with 1 ml of 0.5% solution for each material).

TABLE 21

15 minute % Repellency and 3-hour Contact repellency of *Aedes aegypti*

| Treatment | Concentration (μg/cm$^2$) | % Repellency* | Std. Dev | Sig. Diff. w/Control | Contact Rep.*** w/Control (P value) |
|---|---|---|---|---|---|
| Elemi Essential Oil | 0.5 | 18.0 | 27 | | 0.1143 |
| Amyris Essential Oil (Phoenix NP) | 78.6 | 86.7 | 23 | ** | <0.001 |
| Amyris Essential Oil (EOU) | 78.6 | 27.0 | 29 | | 0.0038 |
| Elemol | 78.6 | 38.9 | 16 | ** | 0.0038 |
| Control | | 2.2 | 15 | — | — |

*% Repellency was determined at 15 minutes.
**Significantly different from control in an LS Mean comparison (α = 0.05).
***Contact repellency was determined as ≧12 in. distance from the treated surface at six time-points over a 3 hour period.
****Concentrations are equivalent to a 0.5% (vol./vol.) solution.

The *Amyris* essential oil from Phoenix NP was highly effective spatially, and elemol was significantly repellent, but not as strongly as the *Amyris* essential oil from Phoenix NP. Elemi oil was tested because it has a small amount of elemol in it, but it was not effective at this low concentration. However, it might be active at a higher concentration, e.g., about 10 times the concentration used herein. The *Amyris* essential oil from EOU was not significantly repellent at this concentration. Three of the materials tested were significantly repellent via the contact repellency mode: both *Amyris* essential oils and the elemol were repellent by contact, while the elemi oil was not.

These results showed that the Phoenix NP *Amyris* essential oil and elemol were still effective at a lower concentration. It is possible, the compounds are effective at even lower concentrations. In actual use, however, higher concentrations will likely be required as the target area will typically be larger than the target area used in these tests.

Example 10

The purpose of this test was to determine the spatial and contact repellency of various biorational agents to the *Culex pipens* mosquito.

Mosquitoes. *Culex pipiens*. Mosquitoes were obtained from the same source as described above.

Starting Materials. The catnip was prepared as described above

Siam Wood. was obtained from Oshadhi Limited, having offices in Petaluma, Calif.

Test Methods. The test methods as described in Example 1. Also only three replications were used instead of six.

Results. Table 22 shows 15-minute repellency and contact repellency to Siam wood essential oil, Siam wood essential oil/catnip essential oil mixture and solvent only control. Using mean values and their related Standard Error of the Mean values (SEM), repellency of the selected samples was determined as shown in Table 22.

Figure 13:
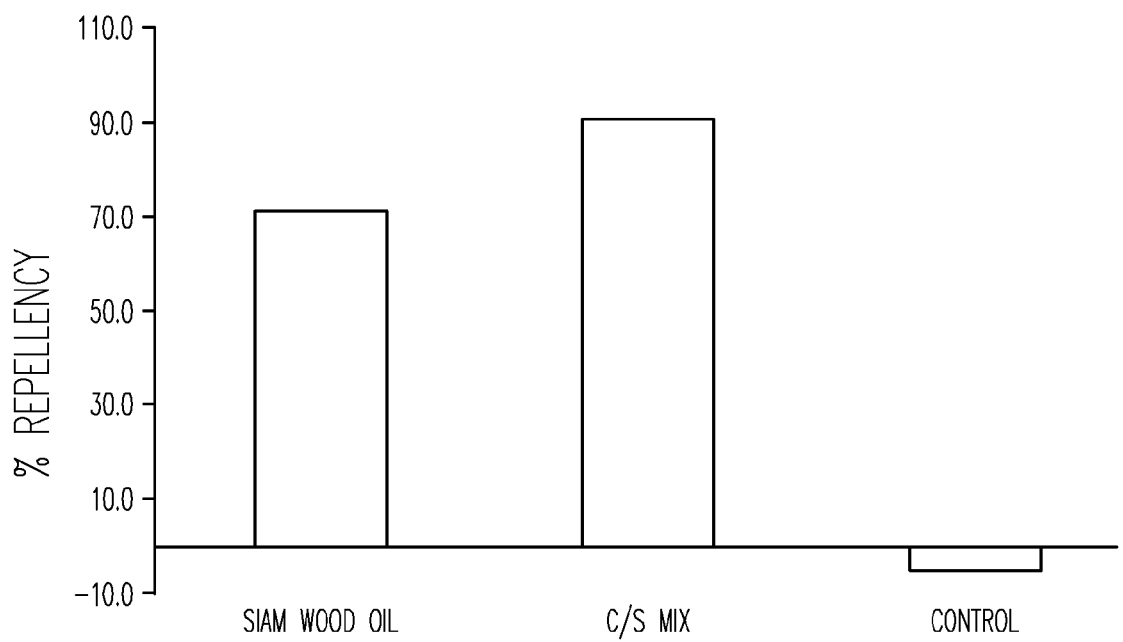
FIG. 13 shows percentage repellency (15 minutes) of adult female yellow fever mosquitoes, Aedes aegypti, measured in three replications in a static-air repellency chamber to Siam wood essential oil, Siam wood essential oil/catnip essential oil mixture and solvent only control, in embodiments of the present invention.

FIG. 13 shows percentage repellency (15 minutes) of adult female yellow fever mosquitoes, *Aedes aegypti*, measured in three replications in a static-air repellency chamber to Siam wood essential oil, Siam wood essential oil/catnip essential oil mixture and solvent only control.

TABLE 22

15-minute repellency and contact repellency

| Treatment | Concentration (%) | Average Percentage Repellency | SEM |
|---|---|---|---|
| Siam wood essential oil | 1 | 71 | 14 |
| Siam wood essential oil and Catnip essential oil (1:1) | 1 | 90.5 | 5 |
| Control | — | −4.8 | 17 |

As Table 22 shows that Siam wood essential oil is quite effective in repelling the mosquitoes, but even more repellent when it is mixed with catnip essential oil. Additional testing will determine the repellency of the individual components of Siam wood essential oil, including the two major components namely, nerolidol and fokienol. Yet other additional testing will include the individual components of catnip oil, namely Z,E-nepetalactone and Z,E-nepetalactone. Other mixtures having varying proportions of the two compounds will also be tested.

CONCLUSION

All publications, patents and patent documents are incorporated by reference herein, as though individually incorporated by reference, each in their entirety, as though individually incorporated by reference. In the case of any inconsistencies, the present disclosure, including any definitions therein, will prevail.

Although specific embodiments have been illustrated and described herein, it will be appreciated by those of ordinary skill in the art that any arrangement that is calculated to achieve the same purpose may be substituted for the specific embodiment shown. This application is intended to cover any adaptations or variations of the present subject matter. For example, although the embodiments focus on repellents, it is possible, that some embodiments may be formulated to kill the target pest, such that the repellent is effectively acting as a pesticide. Therefore, it is manifestly intended that embodiments of this invention be limited only by the claims and the equivalents thereof.

The invention claimed is:

1. A repellent composition comprising an effective repellent amount of *Amyris* essential oil to repel a target pest from a target area, the sesquitepernoid in combination with a carrier, wherein the carrier is a lotion or cream and the *Amyris* essential oil contains over 50%, by weight, of a combination of elemol and eudesmol.

2. The composition of claim 1 wherein the carrier is a solid or liquid.

3. The composition of claim 1 wherein the target pest is an arthropod selected from cockroaches, mosquitoes, black flies, house flies, gnats, stored grain pests, moths, ticks, mites and spiders.

4. The composition of claim 3 wherein the target area is a human or animal.

5. The composition of claim 3 wherein the target area is out-of doors or indoors.

* * * * *